US005605885A

United States Patent [19]
Bernton et al.

[11] Patent Number: 5,605,885
[45] Date of Patent: Feb. 25, 1997

[54] METHOD FOR STIMULATING THE IMMUNE SYSTEM

[75] Inventors: Edward W. Bernton, Washington, D.C.; John W. Holaday, Rowayton, Conn.; Henry U. Bryant, Indianapolis, Ind.

[73] Assignee: EntreMed, Inc., Rockville, Md.

[21] Appl. No.: 315,199

[22] Filed: Sep. 29, 1994

Related U.S. Application Data

[60] Continuation of Ser. No. 161,905, Dec. 3, 1993, abandoned, which is a division of Ser. No. 985,434, Dec. 3, 1992, abandoned, which is a continuation of Ser. No. 586,608, Sep. 24, 1990, abandoned, which is a continuation-in-part of Ser. No. 190,568, May 5, 1988, abandoned.

[51] Int. Cl.$^6$ .................... A61K 39/395; A61K 38/00
[52] U.S. Cl. .................................. 514/12; 514/8
[58] Field of Search ........................... 514/8, 12

[56] References Cited

U.S. PATENT DOCUMENTS 4,837,202  2/1989  Edwards, III ........................... 514/885

OTHER PUBLICATIONS

Arruda et al The Chemical Abstract, vol. 106, p. 90, 1987 Abst. No. 61505x.
Kiess et al, The Chemical Abstract, vol. 99, p. 102 1983, abst. No. 82789u.
Nagy, et al., "Immunomodulation by Bromocriptine", *Immunopharmacology*, 6:231–243 (1983).
Palestine, et al., "Bromocriptine and Low Dose Cyclosporine in the Treatment of Experimental Autoimmune Uveitis in the Rat", *J. Clin. Invest.*, 79:1078–1081 (1987).
McCallum, et al., "Metoclopramide Stimulated Prolactin Secretion in Man", *Jce of M*, 42:1148–1152 (1976).
Hiestand, et al., "Prolactin as a modulator of lymphocyte responsivesness provides a possible mechanism of action for cyclosporine", *Proc. Nat Acadmey of Science*, 83:2599–2603 (1986).
Millard, et al., "Cysteamine Induced Depletion of Both Immunological and Biological Prolactin Activity in the Anterior Pituitary and Blood of the Rat", *Endocrinology*, 113:2161–2167 (1983).
Yamauchi, et al., "effect of Metoclopramide on rat Prolactin Secretin In Vivo", *Life Sceinces*, 20:1581–1583 (1977).
Bernton, et al., "Antibody to Mouse Prolactin Inhibits Murine Lymphocyte Responses to T–Cell Growth Factors (TCGF)", presented at the 11th Inter. Res. Congress & 24th Nat. 1. Reticuloendotheial Society, Oct. 17–21, 1987.
Bernton, et al., "Inhibition of Macrophage In Vivo Activation by Pharmacologic Blockade of Prolactin Release", *Leukocytes and Host Defense*, pp. 213–219 (1986).
Mancini, et al., "Effect of Sulpiride on Serum Prolactin Levels in Humans", *J. Clin. Endoc. Metal.*, 48:181–183 (1976).
Connell, et al., "Effect of Low–Dose Dopamine Infusion on Basal and Stimulated TSH and Prolactin Concentrations, in Man", *Clin. Endoc*, 23:185–192 (1985).

Russell, et al., "Prolactin Receptors on Human Lymphocytes and Their Modulation by Cyclosporine", *Biochem. Biophys. Res. Comm.*, 121:899–906 (1984).
Russell, et al., "Prolactin Receptors on Rat Lymphoid Tissues and on a Human T–and B–Lymphocytes: Antagonism of Prolactin Binding by Cyclosporine", *Prolactin, Basic and Clinical Correlates*, pp. 375–384 (1985).
Gahl, et al., "Blunted Prolactin Response to Thyrotropin–Releasing Hormone Stimulation in Cystinotic Children Receiving Cysteamine", *J. Clin. Endocr. Metal.*, 60:793–796 (1985).
Bernton, "Prolactin and Immune Host Defenses", PNEI Perspectives, vol. 2, No. 1, 1989, pp. 21–29.
Hartman, et al., "Inhibition of Lymphocyte Proliferation by Anti–bodies to Prolactin", *The FASEB Journal* vol. 3, pp. 2194–2202 (Aug. 1989).
Dave, et al., "Prolactin binding a capacity, prostaglandin systhesis and fluidity of murine hepatic membranes are modified during pregnancy and lactation", *J. Endocr.*, pp. 99–106.
Russell, et al., "Prolactin–dependent Mitogenesis in Nb 2 Node Lymphoma Cells: Effects of Immuno–Suppressive Cyclopeptides", *J. of Immunology*, vol. 138, pp. 276–284, (Jan. 1, 1987).
Boutin, et al., "Cloning an Expression of the Rat Prolactin Receptor a Number of the Growth Hormone/Prolactin Receptor Gene Family", *Cell Press*, vol. 53, pp. 69–77, (Apr. 1988).
Boutin, et al., "Long Form of Prolactin Receptor In Human Hepatoma and Breast Cancer Cell", *Molecular Endocr.* pp. 1455–1461 (1989).
Bryant, et al., "Cysteamine Produces Dose–Related Bidirectional Immunomondulatory Effects in Mice", *Journal of Pharm. and Exper. Therap.*, vol. 249, No. 2, pp. 424–429 (1989).
Millard, et al., "Cysteamine–induced depletion of somatostatin and prolactin", *Federation Proc.* 44:pp. 2546–2550 (1985).
Bryant, et al., "Immunsuppression Effects of Chronic Morphine Treatment of Rats", *Life Sciences*, vol. 41 pp. 1731–1738.
Huseby, et al., "Ectopic Pituitary Grafts in Mice: Hormone Levels, Effects on Fertility, and the Development of Adenomyosis Ulterv, Prolactinomas, and Mannary Carcinomas", *Endocrinology*, 116:1440–1448 (1985).
Bernton, et al., "Suppression of Macrophase Activation and T–Lymphocyte Function in Hypoprolactinemic Mice", *Science* vol. 4, pp. 401–404 (Jan. 1988).

(List continued on next page.)

*Primary Examiner*—Howard E. Schain
*Assistant Examiner*—P. Lynn Touzeau
*Attorney, Agent, or Firm*—Jones & Askew

[57] ABSTRACT

The present invention includes methods and compositions for affecting the immune system in animals and humans. The methods and compositions include the administration of prolactin agonists to an immunosuppressed animal or human thereby stimulating the immune system. In addition, the present invention includes a vaccine adjuvant comprising the administration of a prolactin agonist with the vaccine.

20 Claims, 15 Drawing Sheets

OTHER PUBLICATIONS

Hellhammer, et al., "Neurobiological Approaches to Human Disease", Library of Congress pp. 289–300 (1988).

Bernton, et al., "Pharmologic Manipulation of Pituitary Prolactin Secretion Modifies Lymphocyte Function in Mice".

Bernton, et al., "Suppression of Prolactin by Drugs: An IATrogenic Cause of Immunosuppression".

Jaroff, *Time* "Stop That Germ", pp. 56–64, May 25, 1988.

Cooke et al., "Human Prolactin: DCNA Structural Analysis and Evolutionary Comparison", *The Journal of Biological Chemistry*, vol . 256, No. 8, pp. 4007–4016 (Apr. 25, 1981).

Nicoll et al., "Structural Features of Prolactins and Growth Hormones that can be Related to Their Biological Properties", *Endocrin Reviews*, vol. 7 No. 2, pp. 169–203 (1986).

Cunningham et al., "Engineering Human Prolactin to Bind to the Human Growth Receptor," *Science Reports*, vol. 247, pp. 1461–1464 (Mar. 23, 1990).

Cunningham et al., "Zinc Mediation of the Binding of Human Growth Hormone to the Human Prolactin Receptor," *Science Reports*, vol. 250, pp. 1709–1712 (Dec. 21, 1990).

Rozakis–Adcock et al., "Mutational Analysis of the Ligand–Binding Domain of the Prolactin Receptor", *The Journal of Biological Chemistry*, vol. 266, No. 25, pp. 16472–16477 (Sep. 5, 1991).

Paris et al., "Bacterial Production and Purification of Recombinant Human Prolactin", Biotecnol. Appl. Biochem., vol. 12, No. 4, pp. 436–449 (1990).

METHOD FOR STIMULATING THE IMMUNE SYSTEM

CROSS REFERENCE TO RELATED APPLICATIONS

This is a continuation of U.S. application Ser. No. 08/161,905, filed Dec. 3, 1993, which is a divisional of U.S. application Ser. No. 07/985,434, filed Dec. 3, 1992, both now abandoned, which is a continuation of U.S. application Ser. No. 07/586,608, filed Sep. 24, 1990, now abandoned, which is a continuation-in-part of U.S. application Ser. No. 07/190,568, filed May 5, 1988, now abandoned.

TECHNICAL FIELD

The present invention relates to methods and compositions for affecting the immune system in animals and humans and more particularly relates to methods and compositions for enhancing the immune system by regulating the blood levels of the hormone prolactin and certain proteins and peptides with prolactin-like activity.

BACKGROUND OF THE INVENTION

The term "prolactin agonist" as used herein means any compound that has prolactin-like activity, or which increases the number of lactogenic (prolactin-recognizing) receptors on cells. This includes, but is not limited to, prolactin, peptide sequences from prolactin that have prolactin-like activity, growth hormone, peptide sequences from growth hormone which have prolactin-like activity, placental lactogens, and any genetically engineered protein sequence which has prolactin-like activity, or which up-regulates or stimulates lactogen receptors when administered to the intact animal.

The immune system is a highly complex system of cells and tissues that require the cooperation and interaction of a large number of different cell types. The systems of the body comprising the immune system network have been characterized as belonging to the hematopoietic system, the reticuloendothelial or phagocytic system and the lymphoid system.

The hematopoietic system is located in the bone marrow and is responsible for supplying the various precursor and accessory cells of the immune system. The reticuloendothelial system is comprised of the phagocytic cells responsible for destroying or neutralizing foreign substances that may have entered the body. The lymphoid system is comprised of lymphocytes and is responsible for the overall regulation of the immune system and the production of antibodies. Certain cells of the immune system also can secrete factors which greatly augment phagocytic cell function.

The main tissues of the lymphoid system involved in the immune response include the bone marrow and the thymus. Marrow fills the central core of nearly all bones in mammals. The bone marrow contains hematopoietic tissue which is responsible for the formation of erythrocytes, platelets, granulocytes and monocytes and lymphocyte precursors. The thymus is a pouch of epithelial cells filled with lymphocytes, nourished and drained by the vascular and lymphatic systems and innervated by the autonomic nerves. The human thymus is a fully developed organ at birth and weighs 15 to 20 grams. By puberty, it weighs approximately 40 grams, after which it atrophies or involutes as age progresses.

Lymphocytes can be generally classified as either T-lymphocytes or B-lymphocytes. While all lymphocytes are derived from stem cells in the bone marrow, these lymphocyte precursors circulate in the blood through the various organs. Lymphocytes that pass through the thymus become differentiated into either T or B lymphocytes and acquire special functions associated with this differentiation. Most B-lymphocytes have a short life span of approximately 5–7 days and are responsible for the production of antibodies in response to challenge by a particular antigen. T-lymphocytes are smaller than B-lymphocytes and have a life span measured in months or even years. T-lymphocytes are responsible for the general regulation of the immune system and are the principal mediators in cell-mediated immune responses.

B-lymphocytes respond to immunologic phenomena very differently from T-lymphocytes in practically every instance. B-lymphocytes synthesize specialized antibodies in response to the presence of a specific antigen. Specific subtypes of "T"-lymphocytes can augment or suppress this function. Subsequent introduction of the same antigen causes a rapid production of large amounts of the specific antibody causing a rapid elimination of the disease-causing substance.

When T-lymphocytes contact a recognizable antigen in the appropriate context, they pass through a phase of growth and cell division known as lymphocyte transformation or proliferation. This transformation causes the specific, antigen-recognizing T-lymphocytes to produce a large population of their own kind. The antigen is recognizable to a T-lymphocyte only after it has been "processed" by macrophages and properly presented to the T-lymphocyte.

The term "cell-mediated immunity" is used to refer to killing of tumor cells or pathogenic microorganisms either directly by activated "T"-lymphocytes, or by augmented phagocytic cell function resulting from proliferation and secretion of soluble "activation factors" by T-lymphocytes recognizing a specific antigen. This is in contrast to "humoral immunity" which refers to the protective effects of specific antibody secreted by "B"-lymphocytes.

Suppression of the immune system is a clinical disorder found in patients having a variety of illnesses. For example, an increase in the incidence of infectious disease has been reported in chronic narcotic users, such as opioid addicts. These addicts appear to have a reduction of T-lymphocyte number and function. In animal models, treatment with opioids has been shown to inhibit lymphocyte proliferative responses, natural killer cell activity, antibody production and circulating levels of interferon. (See Bryant, Henry U. et al., Immunosuppressive Effects of Chronic Morphine Treatment in Mice, *Life Sciences*, 41:17311 738, 1987).

Cancer patients often exhibit a suppressed immune response. This immunosuppression is most likely caused by agents used to treat the cancer as well as by factors secreted by the cancer cells themselves. Most anti-cancer agents, such a radiation therapy and chemotherapy, inadvertently destroy lymphocytes and other cells important to the immune system. Some tumors, such as the tumors in Hodgkin's disease, release or induce the release of immunosuppressive factors. Hodgkin's disease patients exhibit an abnormally high sensitivity to intracellular parasitic infections such as tuberculosis and herpes virus infections.

Critically ill patients, such as those with severe burns or complications of sepsis or of multiple trauma, many of whom have been treated with dopamine infusions, often demonstrate suppressed immune function, particularly of cell-mediated immunity. Dopamine is normally administered to patients suffering from hemodynamic imbalances caused by shock syndrome due to disorders such as myocardial infarctions, trauma, endotoxic septicemia, open heart surgery, renal failure and congestive heart failure.

Chronic severe stress has also been associated with depressed immune function. As an example, lymphocytes isolated from individuals exposed to psychosocial stress, such as bereavement, appear to proliferate subnormally, resulting in an impaired immune response. (See Schleifer, S. J., et al., Suppression of lymphocyte stimulation following bereavement, *JAMA*, 250:374–377 (1983)) Another case of stress-induced immunosuppression can be found in burn patients. The combination of an ineffectual skin barrier to airborne infections in combination with stress-induced immunosuppression could be the cause of a high mortality rate among these patients.

It is believed the impaired immune response associated with stress is due, in part, to an increased secretion of adrenal corticosteroids from the adrenal glands in response to the stress. However, research has indicated that immunosuppression caused by stress is not solely due to the elevated levels of corticosteroids. A similar suppression of lymphocyte proliferative response in rats following repeated foot shock is evident even after the adrenal glands have been surgically removed.

Patients are often treated with high doses of adrenal corticosteroids or synthetic analogs for several days, or are treated with moderate doses for a longer period of time, to reduce inflammation due to disorders such as inflammatory bowel disease, brain edema secondary to tumor, surgery, or radiation therapy and severe asthma. As described above, the resulting elevated levels of corticosteroids often result in the impairment of immune function as an unwanted side-effect.

The mechanism resulting in immunosuppression by corticosteroid hormones is still poorly understood. Direct toxicity to immune cells and their precursors is not seen at the doses of corticosteroids used clinically. While corticosteroids are known to suppress production of immune cell growth factors such as interleukin-2 when added to cultured lymphocytes, this effect only partially accounts for the suppressive effects they have in the whole animal. We have found that down regulation of prolactin receptors by corticosteroids probably is a major mechanism by which, in the intact animal, they suppress immune function (see below in Detailed Description of Invention and below, Examples 10, 11, and 12). This discovery underlies the efficacy of the present invention in the particular use of preventing glucocorticoid immunosuppression, inasmuch as it has been found the invention can prevent this down-regulation of prolactin receptors.

Patients who receive exogenous adrenal corticosteroids or synthetic analogs for extended periods of time often develop an impaired ability to secrete endogenous steroid hormones, such as cortisol, due to marked atrophy of the adrenal cortex. When these patients are taken off the exogenous hormone therapy, they can suffer from adrenal insufficiency. Such an insufficiency can be detrimental to patients having an infection, recovering from surgery, or suffering from other stresses because these circumstances give rise to an increased demand for adrenal cortical hormones.

What is needed is a composition that will safely and effectively modulate the immune or adrenal systems of an animal or human to prevent the deleterious effects of stress or corticosteroid-treatment on their function, or to stimulate immune, or bone marrow function when it is impaired due to accidental or therapeutic exposure to radiation or to toxins. Such a composition would preferably be a natural substance to reduce the possibility of adverse side effects.

SUMMARY OF THE INVENTION

The present invention comprises treating a human or animal that is immunosuppressed with proteins, peptides and compounds that have prolactin-like activity including, but not limited to, prolactin, peptide sequences from prolactin that have prolactin-like activity, growth hormone (a structurally similar and biologically related hormone), or peptide sequences from growth hormone which have prolactin-like activity, placental lactogens, and any genetically engineered protein sequence which has prolactin-like activity.

The present invention comprises a method for the stimulation of a suppressed or deficient immune system by regulating the blood levels or activity of the hormone prolactin, including, but not limited to, antagonizing suppression of immune function by chronic stress or by treatment with glucocorticosteroids.

The present invention further comprises a method of treating patients to enhance immunosuppression as required for treatment of autoimmune disease or for organ transplants. This method involves treatment with any recombinant engineered protein consisting of the prolactin or growth hormone binding domain, or extracellular domain, in soluble form, of the prolactin receptor molecule. The entire receptor molecule has recently been cloned and sequenced in the rat and human species. (See Boutin, J. M., *Molecular Endocrinology*, Vol. 3, page 1455 (1989), and Boutin, *Cell*, Vol. 53, page 69 (1988)). Because the prolactin receptor binds human prolactin and growth hormone with equal affinity, such a soluble prolactin or growth hormone-binding receptor fragment, would act to bind with high affinity and neutralize the prolactin or growth hormone molecules thereby antagonizing their stimulatory effects on immune function, and resulting in immunosuppression.

It is also contemplated as part of the present invention a method of treating an immunosuppressed human or animal by injecting an effective amount of prolactin or prolactin-like compound thereby causing the immune system of the immunosuppressed human or animal to be stimulated.

According to the present invention, prolactin levels of an immunosuppressed human can be elevated by the administration of purified prolactin obtained from another species, such as sheep, or the administration of human prolactin. Prolactin and growth hormone are normally secreted in a pulsatile fashion, and serum levels can vary rapidly. However a "normal" serum prolactin level in a human male is usually less than approximately 2 ng/ml and in a nonpregnant female, less than 8 ng/ml. The human prolactin can be natural human prolactin isolated from the human pituitary gland or preferably prolactin that is synthesized by recombinant DNA techniques.

It is also contemplated in the present invention that the effective prolactin levels in the blood can be raised by administration of that portion of the prolactin molecule that has immunoregulatory activity, including such portion manufactured by recombinant DNA technology. Human or animal growth hormone, manufactured by recombinant DNA technology, or the active protein fragment, could also be administered to increase levels of prolactin-like activity. For human medical use, prolactin rather than growth hormone is a preferred embodiment of this invention because growth hormone could have unwanted metabolic side-effects such as stimulation of bone growth and antagonism of insulin action (diabetogenic effect) at the doses contemplated for treatment.

Alternatively, prolactin levels can be increased by the administration of a substance, such as cysteamine, that will, at a low dose, stimulate the secretion of endogenous pituitary prolactin. Dopamine receptor type-2 antagonists, designed to act selectively and not affect the central nervous system, can also be used to stimulate pituitary prolactin secretion. Administration of a pituitary prolactin releasing factor can also be used to stimulate endogenous prolactin secretion. Peptides or organic drugs which are designed to act as prolactin agonists upon the immune system without causing an effect on the reproductive system would also be useful immunostimulants and are contemplated as part of the present invention.

It is contemplated in the present invention that prolactin or a prolactin like compound can be used as a vaccine adjuvant. Because prolactin enhances the immune activity of a human or animal, if prolactin is administered either with a vaccine or soon before or after administration of the vaccine, the human or animal will respond more strongly to the antigen in the vaccine. This is particularly important with many new vaccines using synthetic peptides or recombinant DNA manufactured protein antigens which are very pure but often poorly antigenic (i.e. recombinant HIV vaccine candidate proteins and peptides).

It is further contemplated that the prolactin could be modified so that it has a longer blood half-life then the native protein, such as by covalent attachment of ethylene glycol. It is also contemplated that a parenteral sustained release dosage form of prolactin-like hormone would be the most effective form of this invention.

Accordingly, it is an object of the present invention to regulate a depressed or insufficient immune system by increasing the amount of prolactin or prolactin-like substance in the body of a patient.

It is a further object of the present invention to prevent impairment of adrenal cortical secretory function occurring following medical treatment with corticosteroids by increasing the level of prolactin or prolactin-like substance in the body.

It is a further object of the present invention to increase prolactin levels by the administration of purified prolactin, either from human or animal sources.

It is a further object of the present invention to increase prolactin levels by the administration of recombinant human prolactin prepared by recombinant DNA technology.

It is a further object of the present invention to increase growth hormone levels by the administration of recombinant human growth hormone prepared by recombinant DNA technology, which would serve to upregulate prolactin receptors and stimulate immune function.

It is a further object of the present invention to increase prolactin levels by stimulating the secretion of endogenous pituitary prolactin.

It is yet another object of the present invention to provide a treatment for stress induced impairment of the immune system.

It is yet another object of the present invention to provide an improved method of producing monoclonal antibodies by elevating the immune response of the mouse or polyclonal antibodies, by elevating the immune response of the horse, goat, rabbit, mouse or other immunized animal, by pretreatment with prolactin or with a prolactin-like hormone or prolactin agonist.

It is another object of the present invention to provide a method a treating livestock for shipping fever, by treating with prolactin, growth hormone, or other prolactin agonist during or prior to this stress.

It is a further object of the present invention to provide a method of stimulating the immune system after treatment of inflammation with steroids.

It is another object of the present invention to provide a vaccine adjuvant.

It is yet another object of the present invention to provide a method of increasing the immune response during mass immunizations during war or natural disasters.

It is a further object of the present invention to provide a novel method of immunosuppression for use in autoimmune disease or transplantation where cysteamine chloride is administered at doses wherein the serum levels of prolactin are decreased and prolactin receptors are down regulated and thereby provide therapeutic immunosuppression.

It is a further object of the present invention to provide a novel method of immunosuppression for use in auto-immune disease or transplantation where a recombinant DNA engineered soluble hormone-binding fragment of the prolactin receptor is administered at adequate doses to decrease free serum prolactin or growth hormone levels and down regulate prolactin receptors and thus provide therapeutic immunosuppression.

These and other objects, features and advantages of the present invention will become apparent after a review of the following detailed description of the disclosed embodiment and the appended claims.

DETAILED DESCRIPTION OF THE INVENTION

Figure 1:
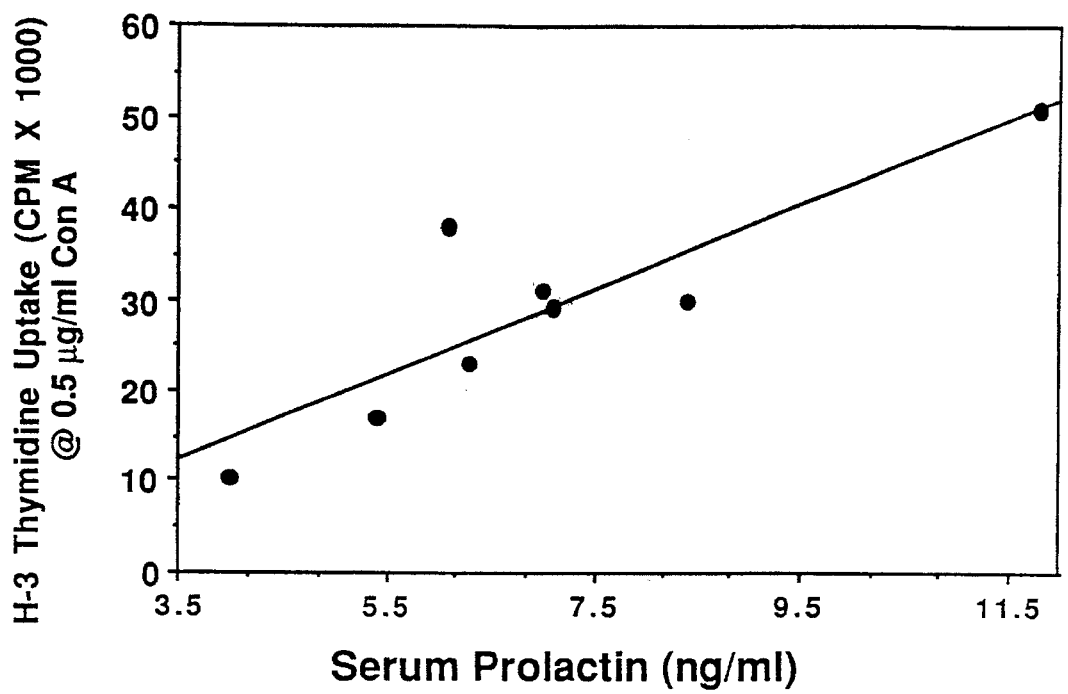
FIG. 1 shows tritiated thymidine uptake in spleen cells incubated with concanavalin A from mice treated with different doses of cysteamine.

The present invention comprises a method for the stimulation of a suppressed or deficient immune system by regulating the blood levels or actions of the hormone prolactin. The present invention also comprises treating a human or animal that is immunosuppressed using proteins, peptides and compounds that have prolactin-like activity including, but not limited to, prolactin, peptide sequences from prolactin that have prolactin-like activity, growth hormone, peptide sequences from growth hormone which have prolactin-like activity, placental lactogens, and any genetically engineered protein sequence which has prolactin-like activity.

Prolactin-like activity is defined, for the purposes of this invention as the ability of a drug or natural or recombinant DNA manufactured hormone to: 1) up-regulate expression of prolactin receptors when administered to the whole animal, or 2) to stimulate growth of the NB-2 rat lymphoma cell line, a standard bioassay for prolactin activity, or 3) to substitute for prolactin to support mammalian lactation, and either a) stimulate the proliferative responses of spleen or peripheral blood lymphocytes co-cultured with mitogens following 72 hours of continual hormone or drug administration (i.e. in laboratory mice); or b) reverse the suppression of lymphocyte proliferative responses to mitogens in spleen lymphocytes of mice treated simultaneously with 125 µg/day of corticosterone and a reasonable dose (5 to 200 µg/day) of the prolactin-like protein or the prolactin agonist drug.

The present invention involves the manipulation of in vivo concentrations of prolactin to effect modulation of the immune response. By increasing the level of prolactin in immunodepressed individuals, the immune system can, in many cases, be stimulated to achieve normal levels of responsiveness and effectively combat disease. Likewise, by causing a decrease in the prolactin level of an individual with disease due to an abnormal autoimmune response, immune function can be restored towards normal.

The level of prolactin or prolactin agonist activity in humans can be increased in various ways. The preferred method of increasing prolactin blood levels is by direct administration of prolactin from another source, such as purified prolactin from animal or human sources or recombinant prolactin (i.e., prolactin produced by recombinant DNA techniques). This exogenous prolactin is preferably administered intramuscularly or subcutaneously at a dose of between approximately 0.01 and 0.2 mg per kilogram body weight per day, but it is to be understood by one of ordinary skill in the art that other methods of administration may be equally effective.

Recombinant human or bovine growth hormone, also has prolactin-like activity as defined above, and would preferably be administered intramuscularly or subcutaneously at a dose of from 0.01 to 0.5 mg per kilogram per day.

It is believed that sustained and continual release of small quantities of prolactin, growth hormone, or other prolactin-like protein are maximally effective in stimulating immune, hematopoietic, or adrenal function, and at upregulating prolactin receptors. It is further contemplated that the prolactin or prolactin agonist could be modified so that it has a longer blood half-life than the native protein, such as by covalent attachment of ethylene glycol. It is also contemplated that a parenteral sustained release dosage form of prolactin-like hormone would be the most effective form of this invention. For veterinary use in larger food animals, it is contemplated that a pellet of recombinant prolactin or prolactin-like protein compounded in a matrix of cholesterol and methyl-cellulose for delayed absorption could be implanted subcutaneously in the animal's ear. For human medical use, it is contemplated that prolactin can be incorporated in a polyvinylproline or other biodegradable, inert, and absorbable polymer for sustained release from a subcutaneous implant, or by absorption from a buccal (placed between lip and gum) mucosal patch or formulated with a carrier such as DMSO for transcutaneous absorption from an adherent skin patch.

It is to be understood by one with ordinary skill in the art that such compounding methods are not proprietary or original and that other methods to achieve implantable biocompatible preparations of these compounds for sustained parenteral release at effective dosages may be equally efficacious.

An alternative method of increasing prolactin levels to enhance the immune responsiveness of the immunosuppressed individual is to administer a substance that will stimulate the secretion of endogenous pituitary prolactin. Low doses of cysteamine (approximately 1 to 25 mg per kg body weight per day) increase prolactin secretion and thereby cause the desired immunostimulating effect. Preferably, the salt, cysteamine HCl, is administered orally once or twice each day to achieve adequate immunostimulation. Cysteamine (2-aminoethanethiol) is a sulfhydryl reducing agent used clinically to elevate hepatic stores of glutathione in the treatment of acetaminophen toxicity and in the therapy of nephropathic cystinosis.

In contrast, high doses of cysteamine (approximately 50–500 mg per kg body weight) decrease prolactin secretion thereby causing a depression of the immune system. It is believed that these doses of cysteamine also down-regulate or otherwise impair function of the prolactin receptor. High doses of cysteamine are therefore useful in the treatment of autoimmune diseases such as arthritis and lupus erythematous. High doses of cysteamine are also useful in reducing the rejection of transplanted tissue or organs in animals or humans. It is contemplated as part of the present invention that the cysteamine treatment would be started prior to the transplantation of the organ and would be maintained after the tissue has been transplanted into the human or animal.

Peripherally acting dopamine receptor type-2 antagonists, such as metaclopromide and domperidone, stimulate pituitary prolactin secretion with minimal effects on the central nervous system. Preferably, an intravenous or oral dose of approximately 5 to 20 mg of the antagonists is administered to an immunodepressed patient twice each day to enhance immune responsiveness. Dopamine antagonists are particularly useful in the treatment of critically ill patients who have received dopamine infusions because dopamine potently suppresses secretion of the pituitary hormone prolactin.

An intramuscular dose of approximately 0.1 to 2.0 mg of the neurophysin fragment known as the pituitary prolactin releasing factor (or glycopeptide 1–39) can also be an effective stimulant of prolactin secretion. This factor, also known as Posterior Pituitary Natriuretic Factor, normally contains the amino acid sequence Leu-Gln-Pro-Gly-Val-Leu or a significant portion of the above-described amino acid sequence. It will be understood by those of ordinary skill in the art that any structural analog of the described amino acid sequence could also stimulate pituitary prolactin secretion.

Peptides and organic drugs which act as a prolactin agonist upon the target tissues of the immune system can also be used to enhance the depressed immune system. While the administration of exogenous prolactin or the stimulation of endogenous prolactin may, over longer periods have an effect on other systems of the body such as the reproductive system, these peptides and organic drugs can mimic the immunostimulatory effects of prolactin selectively, without causing an adverse effect upon the reproductive system.

Another embodiment of the present invention is the use of prolactin or prolactin-like compounds as an adjuvant for vaccines. According to the present invention, prolactin or prolactin-like compounds can be admixed with or co-administered with a conventional vaccine and administered to the human or animal to increase the immune response to the vaccine. It is important to note that the prolactin or prolactin-like compounds can be administered either before, during or after the vaccine is administered to the human or animal.

In a preferred embodiment of this invention, a sustained-release form of prolactin or growth hormone or prolactin agonist such as described above could be administered once at the time of immunization and maintain therapeutic levels of the hormone for the 3 to 5 day period required to optimally modulate the immune response. A single dose of soluble protein is less effective because of the short (approximately 20 minute) circulating half-life of these hormones. Use of the present invention is especially beneficial in mass immunizations, e.g., during war time or during natural disasters when deficient immune responses due to chronic stress are more common. However, it is to be understood that practicing the present invention of administering prolactin to a normal individual will potentiate the antibody response in normal individuals.

A specific example of a poorly antigenic vaccine would be human hepatitis B vaccine, where three immunizations spaced 6–12 weeks apart are necessary to obtain protective immunity. Administration of recombinant prolactin or growth hormone prior to vaccination results in more rapid acquisition of effective immunity.

The present invention is also especially beneficial for treating humans or animals with illnesses such as asthma, inflammatory bowel disease, cerebral edema due to tumors, parasitic diseases and arthritis and being treated with corticosteroid therapy. Any condition wherein the immune system is suppressed either naturally or as the result of administration of steroidal antiinflammatory agents can benefit from application of the present invention.

As a second preferred embodiment of the present invention, natural or recombinant prolactin, endogenous prolactin secretion stimulants, and selective prolactin agonists can be used to prevent the impairment of adrenal cortical secretory functions in patients that have been chronically treated with exogenous glucocorticosteroids or synthetic analogs.

As the third preferred embodiment of the present invention, the use of prolactin, growth hormone, prolactin-agonists or stimulants of prolactin secretion can be used to accelerate the recovery of hematopoietic and lymphopoietic function of the bone marrow of an individual with bone marrow function (production of formed blood elements) suppressed due to accidental radiation or toxin exposure or medical treatment with radiation or anti-neoplastic drugs.

The present invention also includes the use of prolactin or prolactin-like compounds in veterinary medicine. For example, the administration of prolactin or prolactin-like compounds to animals before shipping is beneficial for maintaining the immune system in these animals and avoiding the common disease known as shipping fever and thereby preventing the loss of body weight and meat product value.

Although not wanting to be bound by the following, the inventors believe that sustained, elevated blood levels of prolactin, growth hormone, or prolactin-like protein causes immune system cells, such as lymphocytes, to increase the number of prolactin receptors on the cell membrane. Conversely, administration of corticosteroids greatly decreases the number of prolactin receptors. This decrease is also found when animals are chronically stressed and their increased secretion of adrenal corticosteroids has elevated levels to the high physiologic range. Administration of prolactin or growth hormone can completely prevent this effect of corticosteroids. Doses of prolactin or prolactin agonists which potentiate immune responses result in substantial increases in prolactin receptors. The change in prolactin receptors, as measured in the liver by standard techniques, is found to correlate directly with the change in immune responsiveness following treatment with corticosteroids or prolactin agonists, singly or in combination.

It has been demonstrated that lymphocytes produce an endogenous prolactin-like protein. It is believed that this endogenous prolactin-like protein plays an important role in allowing the proliferation of the lymphocyte. Antibodies to prolactin, added to cultured lymphocytes or bone-marrow cells prevent the cells' proliferation. This endogenous prolactin-like protein may exert its effect on the cell by binding to the prolactin receptors on the cells and this effect is required for cell division and replication. It is believed that the more receptors on the cell, the more pronounced the response is. It is further believed that elevating the blood level of prolactin or prolactin-like substance, modestly, but continually for at least 48 hours causes the cell to produce more prolactin receptors and thereby makes the lymphocyte better able to proliferate in response to immune stimuli. Similarly, it is believed that adequate expression of prolactin receptors (which are abundant in the adrenal cortex) is necessary for the maintenance of adrenal cortical cell mass and steroid synthetic function. Additionally, prolactin receptors on bone marrow stem cells, and their ability to respond to prolactin-like proteins, are essential to allow these cells to replicate and/or differentiate efficiently to supply lymphocytes, monocytes, granulocytes, and red blood cells, although marrow cell prolactin receptors appear less susceptible to down-regulation by corticosteroids (which do not generally suppress hematopoietic function).

It will be understood by those skilled in the art that the present invention could also be used in the treatment of patients suffering from aplastic anemia, in the treatment of patients recuperating from a bone marrow transplant, or in the treatment of patients with suppressed bone marrow function due to exposure to radiation, toxins, or anti-neoplastic drugs.

It will be likewise understood, that a prolactin agonist could be added to conventional infant formulas as a dietary supplement to impart immunostimulant, anti-stress, and anabolic activities for premature neonates who are unable to breastfeed. An example of a conventional infant formula that can be used to practice the present invention includes, for example, Similac-Special Care (Ross Laboratories, Columbus, Ohio). It is to be understood that any conventional infant formula could be used to practice the present invention. When prolactin is used to supplement the conventional infant formula, the preferred concentration of prolactin in the infant formula is between approximately 0.5 and 10 µg/g of infant formula. The present invention also includes a method of feeding a human or animal infant comprising the step of administering to the human or animal a conventional feeding formula supplemented with an effective amount of a prolactin agonist.

Another embodiment of the preferred invention is the administration of the soluble recombinant DNA-expressed binding domain of the prolactin receptor, for the purposes of immunosuppression. This can be combined as adjunctive therapy with standard therapies such as glucocorticosteroids or cyclosporine. This prolactin-receptor derived protein is preferably administered intramuscularly or subcutaneously at a dose of between approximately 0.01 and 0.1 mg per kilogram body weight per day but it is to be understood by one of ordinary skill in the art that other methods of administration are effective.

EXAMPLE 1

Mice treated orally with cysteamine hydrochloride show elevation or suppression of serum prolactin levels. The serum prolactin level correlates directly with the ability of spleen lymphocytes from treated mice to proliferate when co-cultured with the mitogens lipopolysaccharide or concanavalin A.

Methods—Male C3H/HeN mice weighing 20 to 25 g are given various doses of cysteamine HCl. Cysteamine is dissolved in distilled water and given either by subcutaneous injection or by oral intubation 4 hours into the light cycle for three days. Light onset is at 6:00 A.M. each day. The animals are sacrificed on the fourth day. Trunk blood is collected, allowed to clot, and serum is obtained by centrifugation (3,000 rpm for 10 min.). Spleens are aseptically removed and weighed. Thymuses are also removed and weighed. In other experiments, mice are treated with either water, or cysteamine (300 mg/kg) with or without injection of 50 µg of ovine prolactin subcutaneously, every twelve hours, for a 4 day period.

Splenocytes are mechanically dissociated and suspended in RPMI 1640 culture medium (Gibco Laboratories, Grand Island, N.Y.). The splenocytes are then counted and resuspended to a concentration of $4.0 \times 10^6$ cells/ml in RPMI 1640 medium containing 5% fetal calf serum (HyClone Laboratories, Logan, Utah), 12 mM HEPES buffer (Gibco) and 0.05 mg/ml gentamicin (Gibco). Lymphocyte proliferative responses to various concentrations of concanavalin A (Con A; Sigma Chemical Co., St. Louis, Mo.) or bacterial lipopolysaccharide (LPS; from *S. typhimurium*, RIBI Immunochem Research Inc., Hamilton, Mont.) are assessed by aliquoting 100 µl of the cell suspension with 100 µl of mitogen (0.5 to 4.0 µg/ml Con A or 0.2 to 10 µg/ml LPS) to each well of a 96 well multi-tier plate. The stimulated cell suspensions are incubated at 37° C. with 6% $CO_2$ for 24 hours. Each well is then pulsed with 0.5 µCi of methyl-$^3$H-thymidine (NEN Research, Boston, Mass.), and 24 hours later, cells are harvested on glass fiber filters (Skatron Inc., Sterling, Va.) and washed. Liquid scintillation spectrophotometry of the filters provide a measure of the uptake of methyl-$^3$H-thymidine by the lymphocytes in each well. For any given replication of an experiment, two mouse spleens are pooled for each treatment group and triplicate wells are assayed at each concentration of mitogen. Four to eight replications are conducted at each dose of cysteamine.

Serum prolactin levels are monitored by homologous radioimmunoassay (reagents provided by A. F. Parlow, Pituitary Hormones and Antisera Center). Serum corticosterone levels are assessed with a $^3$H-corticosterone radioimmunoassay kit obtained from Radioimmunoassay Systems Laboratories (Carson, Calif.). A 1:250 dilution of mouse serum is used in the assay.

Results—cysteamine both stimulates and suppresses concanavalin A and lipopolysaccharide-induced blastogenesis, depending upon the dose of cysteamine administered. The lowest dose of cysteamine, 12.5 mg/kg, given once per day for three consecutive days results in significant increases in mitogen-induced lymphocyte proliferation, particularly at the lower concentrations of mitogen.

Orally administered cysteamine in mice shows a similar pattern of stimulation of concanavalin A-induced proliferation at the lower doses.

Figure 2:
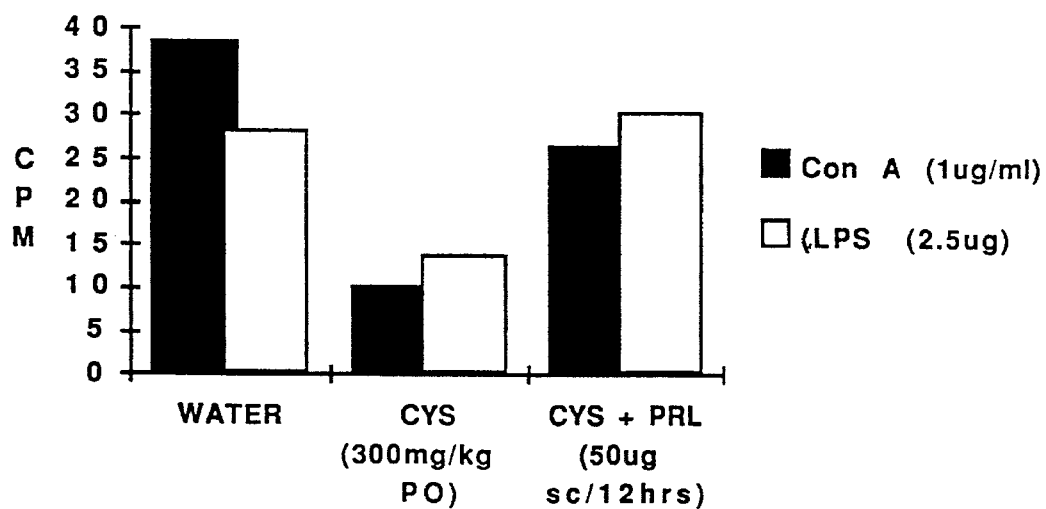
FIG. 2 shows tritiated thymidine uptake in spleen lymphocytes incubated with concanavalin A from mice treated with cysteamine and cysteamine plus prolactin.

Serum prolactin levels are elevated in mice following subcutaneous administration of 12.5 mg/kg cysteamine and suppressed with 400 mg/kg. Mean prolactin levels at each dose of cysteamine are positively correlated ($r=0.907$; $p=0.0024$) with concanavalin A-induced proliferation, as shown in FIG. 2. (Each point on the graph of FIG. 1 represents the mean hormone level and proliferative response to 0.5 µg 1 ml concanavalin A for 6 to 12 mice.)

Treatment with 300 mg/kg of cysteamine significantly suppresses lymphocyte proliferation in response to Concanavalin-A and lipopolysaccharide. This is antagonized by concurrent treatment with exogenous ovine prolactin (FIG. 2).

This experiment reveals that low doses of cysteamine stimulate the immune system by stimulating mitogen-induced blastogenesis in mice. The strong correlation of serum prolactin levels to mitogen-induced proliferation indicates that low doses of cysteamine stimulate the secretion of prolactin from the pituitary and thereby stimulate the immune response.

In FIG. 2, mice are treated with an immunosuppressive dose of cysteamine, with or without concurrent treatment with ovine prolactin. Treatment with ovine prolactin prevents the immunosuppressive effects of cysteamine treatment, suggesting this effect is mediated by the drug's inhibition of prolactin secretion.

EXAMPLE 2

Figure 3:
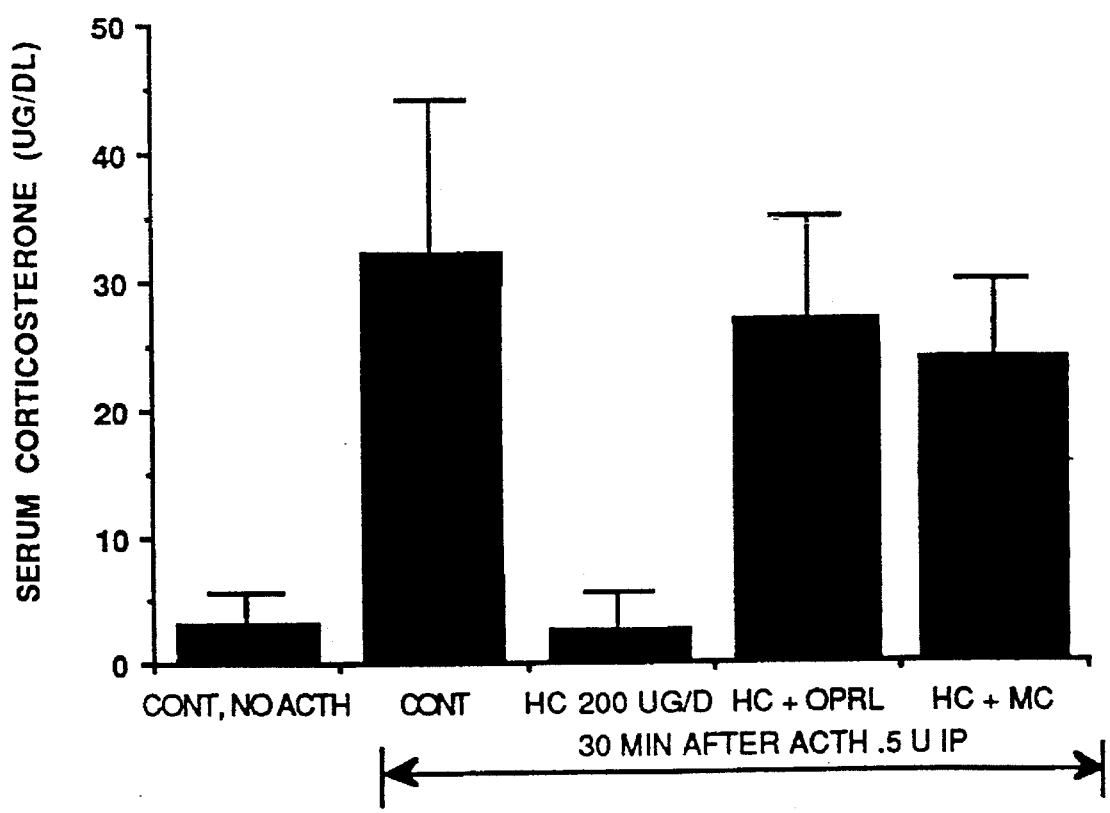
FIGS. 3 and 4 show the effects of hydrocortisone treatments in mice with and without metaclopromide or ovine prolactin.

Groups of five mice are treated with either control vehicle, hydrocortisone 200 µg/day, hydrocortisone and ovine prolactin 125 µg/day, or hydrocortisone and metaclopromide 500 µg/day. After 4 days of treatment, all mice receive 0.5 units of adrenocorticotropic hormone (ACTH) to stimulate adrenal secretion of corticosterone, and blood is drawn thirty minutes later for determination of serum corticosterone. In vehicle treated animals, ACTH causes an almost 10-fold increase in serum corticosterone. This is not seen in animals treated with hydrocortisone, demonstrating the well-known phenomenon of adrenal suppression by exogenous corticosteroids. Animals treated concurrently with hydrocortisone and either prolactin or metaclopromide (which stimulates endogenous prolactin release), show an intact corticosterone secretory response to ACTH. (FIG. 3) Thus, treatment with exogenous prolactin prevents suppression of adrenal cortical function due to treatment with exogenous corticosteroids.

Figure 4:
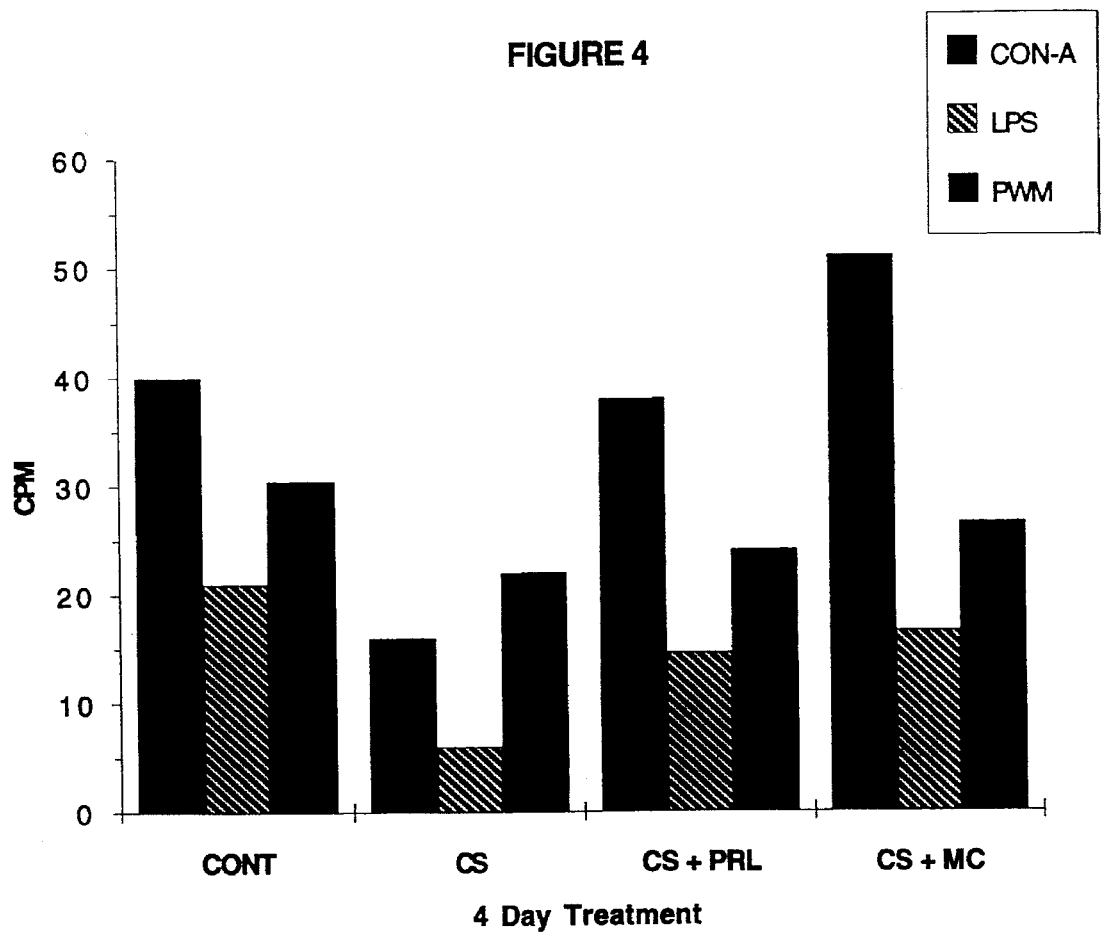

In the same experiment, spleen lymphocytes from the mice in each treatment group are co-cultured with T and B-cell mitogens. Treatment with prolactin or metaclopromide reversed the immunosuppression resulting from hydrocortisone treatment. (FIG. 4) This dose of metaclopromide is shown to cause an approximately 5-fold increase of serum prolactin lasting about 6 hours.

EXAMPLE 3

Groups of 5 mice are implanted with either a 75 mg pellet of morphine sulfate (MS) or a control pellet. Groups also received morphine pellets and daily injections of 500 µg of metaclopromide (MC) and morphine pellets and daily injections with 125 µg of ovine PRL. Spleen lymphocytes are pooled from each treatment group for determination of proliferative responses to the mitogens Concanavalin A (Con-A) and bacterial lipopolysaccharide (LPS).

Figure 5:
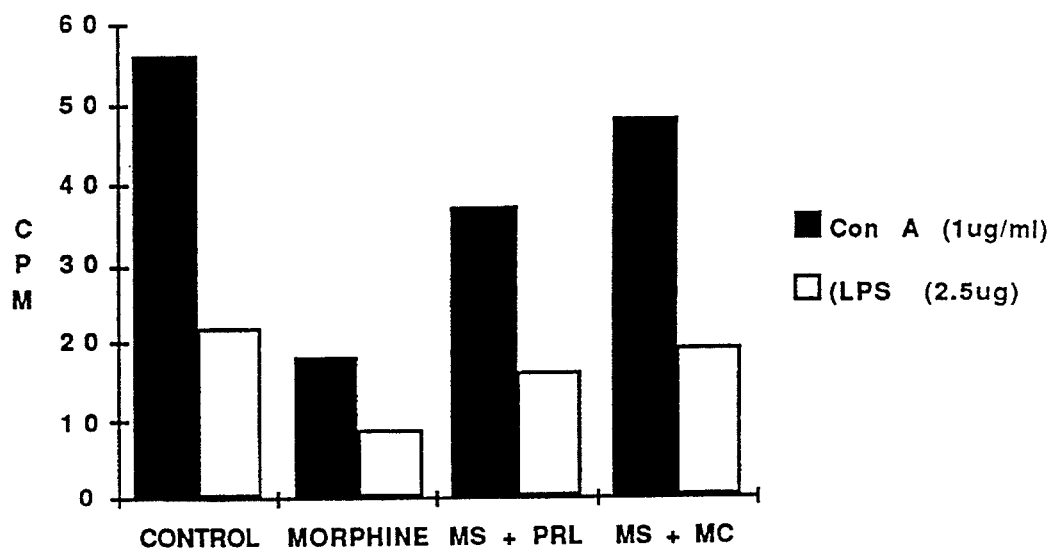
FIG. 5 shows the effect of morphine treatment in mice with and without metaclopromide or prolactin. Spleen lymphocytes were stimulated with lipopolysaccharide or concanavalin A.

Treatment of mice with ovine prolactin or metaclopromide antagonizes the suppression of lymphocyte proliferative responses in mice severely stressed by the subcutaneous implantation of a 75 mg morphine pellet for 48 hours. (FIG. 5) This demonstrates that immunosuppression due to activation of the neuroendocrine stress response to a physiologic and behavioral stressor can be prevented by treatment with exogenous prolactin or with a drug which stimulates secretion of endogenous prolactin.

EXAMPLE 4

Figure 6:
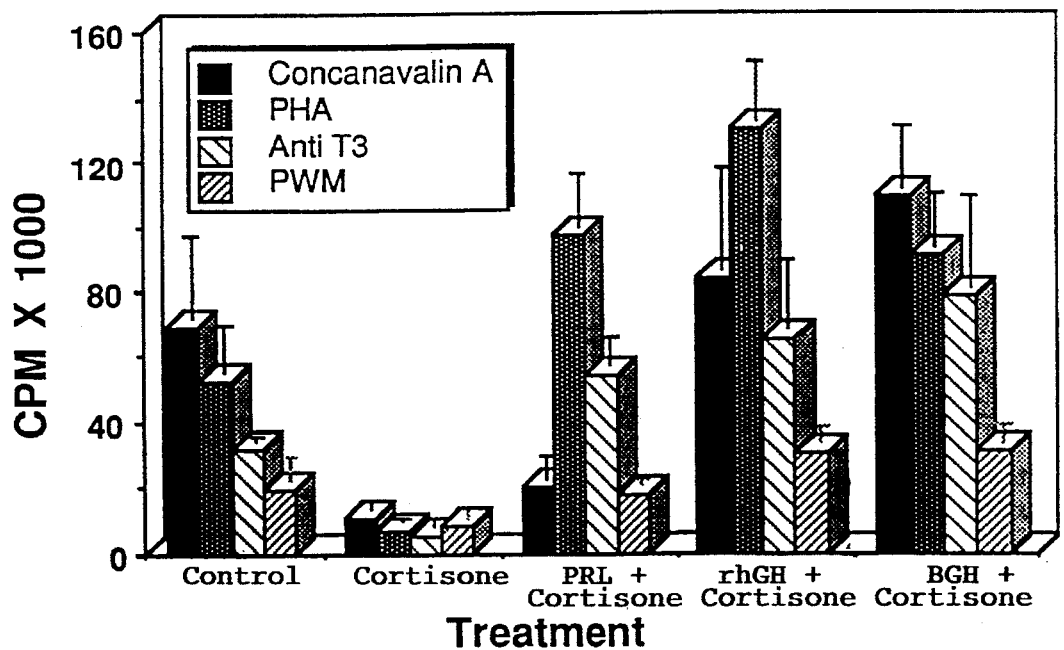
FIG. 6 shows the effect of various prolactin agonists on spleen lymphocytes from cortisone treated mice.

For each treatment three groups of two male C3H/HeN male mice are used. "Cortisone" treated mice are implanted with corticosterone pellets subcutaneously releasing 50 µg/day of steroid, and with Azlet minipumps releasing 1 µl/hr of saline. Other groups are implanted with identical pellets, as well as with Azlet pumps releasing 1 µg/hr of either ovine prolactin, recombinant human growth hormone, or recombinant bovine growth hormone. After 3 days of treatment, mice are sacrificed and spleen cells from each group cultured with the indicated mitogen. Lymphocyte proliferation in response to mitogens is determined by incorporation of tritiated thymidine, and expressed in CPM (thousands). This graph represents the mean and standard errors for each treatment, determined from 3 pools of two mouse spleens per treatment. (FIG. 6)

Treatment of mice with recombinant human growth hormone, recombinant monkey prolactin, and recombinant bovine growth hormone for a period of 72 hours also stimulates lymphocyte proliferation and antagonizes the suppression of lymphocyte proliferation by corticosteroid treatment. This demonstrates that the effect is not due to a contaminant in prolactin from natural sources, that recombinant hormones retain the immunomodulatory activity. Recombinant human growth hormone, as well as recombinant bovine growth hormone (which does not bind at the prolactin receptor) clearly have prolactin-like immunomodulatory activity in vivo. (FIG. 6)

Figure 7:
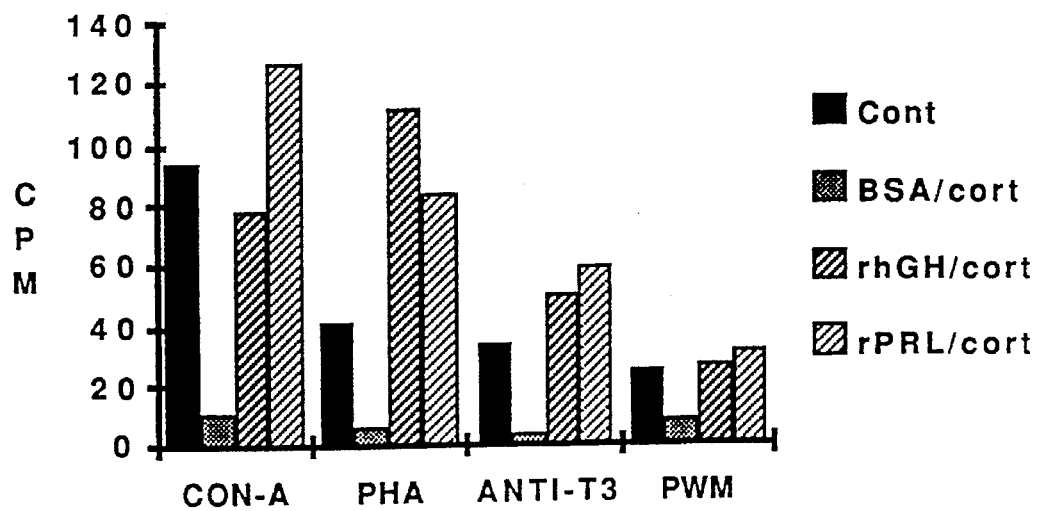
FIG. 7 shows the effect of growth hormone and prolactin on spleen cells from mice treated with corticosterone.

Similar results are obtained in another experiment using recombinant monkey prolactin. (FIG. 7) For each treatment four C3H/HeN male mice are used. "Cortisone" treated mice are implanted with corticosterone pellets subcutaneously releasing 50 µg/day of steroid, and with Azlet minipumps releasing 1 µl/hr of bovine serum albumin (BSA). Other groups are implanted with identical pellets, with the addition of Azlet pumps releasing 1 µg/hr of either recombinant human growth hormone (rhGH), or recombinant monkey prolactin (rPRL). After 3 days of treatment, mice are sacrificed and spleen cells from each group cultured with the indicated mitogen. Lymphocyte proliferation in response to mitogens is determined by incorporation of tritiated thymidine, and expressed in CPM (thousands).

EXAMPLE 5

Figure 8:
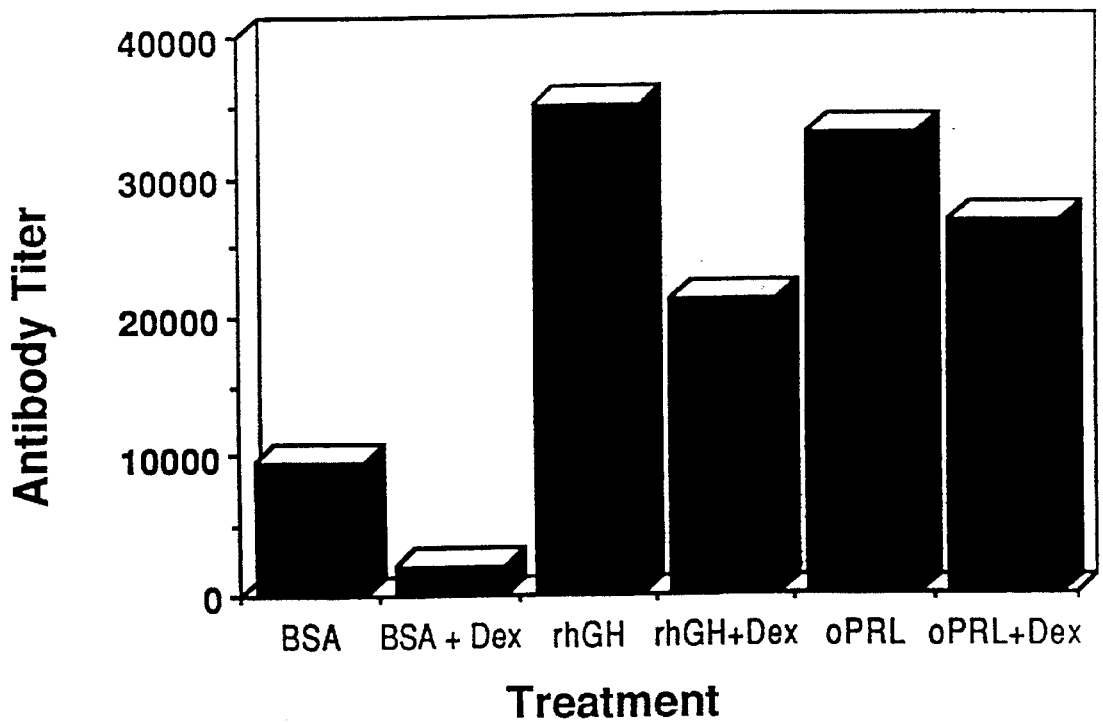
FIG. 8 shows the effect of growth hormone and prolactin on antibody production in dexamethasone treated mice.

Treatment of mice with ovine prolactin or with recombinant human growth hormone during the primary immunization increases serum titers of antibody to tetanus toxoid measured one week after the secondary "booster" immunization with tetanus toxoid. (FIG. 8) Groups of 5 mice are treated days 1 through 4 with either vehicle or 0.4 mg of dexamethasone, sc, every 12 hours. On days 1 through 4 mice also received either bovine serum albumin, recombinant human growth hormone or ovine prolactin, as indicated, 25 µg sc followed by 1 µg/hr infused via subcutaneous Azlet minipump. On day 2 mice are immunized with 4 TU of purified tetanus toxoid, sc at the base of the tail. On day 8 mice received a second immunization with 4 TU of tetanus toxoid. On day 14 mice are sacrificed and bled for determination of IgG anti tetanus antibodies by ELISA. Mean serum antibody titers of groups of 5 mice are shown in FIG. 8.

Figure 9:
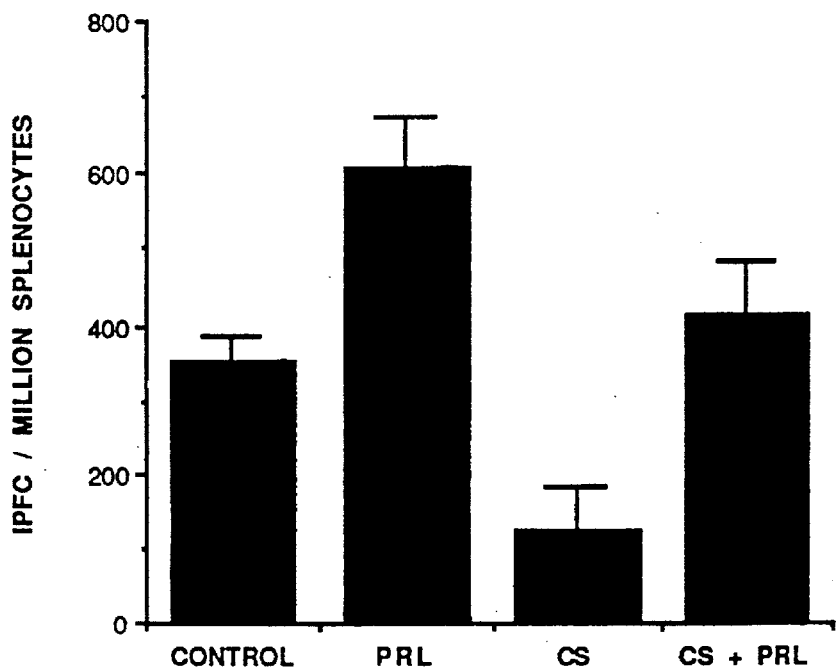
FIG. 9 shows the effect of prolactin on the number of spleen lymphocytes secreting antibodies to tetanus toxoid in mice treated with corticosterone.

Groups of 5 mice are treated days 1 through 4 with either vehicle or 50 µg/day of corticosterone released continually from a pellet implanted subcutaneously. (FIG. 9) On days 1 through 4 mice also received either bovine serum albumin, or ovine prolactin, as indicated, 25 µg subcutaneously followed by 1 µg/hr infused via subcutaneous Azlet minipump. On day 2 mice are immunized with 8 TU of purified tetanus toxoid, intraperitoneally. Five days later mice are sacrificed and spleens disassociated, counted, and adjusted to identical concentrations. Cells are co-incubated with sheep red blood cells which had been tanned and sensitized with tetanus toxoid (Wyeth), using the method of Cunningham and Szenberg. Indirect PFC (IPFCC, IgG) are facilitated by addition of goat anti-mouse IgG antisera. Lytic plaques representing anti-tetanus Ab-secreting lymphocytes are enumerated under a microscope, and expressed per million nucleated spleen cells for each mouse.

The number of spleen lymphocytes secreting antibodies to tetanus toxoid, measured by the indirect hemolytic plaque forming assay five days after immunization with tetanus toxoid, is found to be significantly increased in mice which are treated with either ovine prolactin or recombinant human growth hormone. (FIG. 9) These studies demonstrate the potential adjuvant effect of prolactin like hormones on antibody responses to immunization.

EXAMPLE 6

Groups of 4 mice are injected daily subcutaneously with 0.2 ml saline containing either 0, 50, 100, or 250 of ovine prolactin. After three days of treatment spleen lymphocytes are from each group are pooled and co-cultured with the indicated mitogens and proliferation determined after 48 hours in culture by incorporation of tritiated thymidine.

Figure 10:
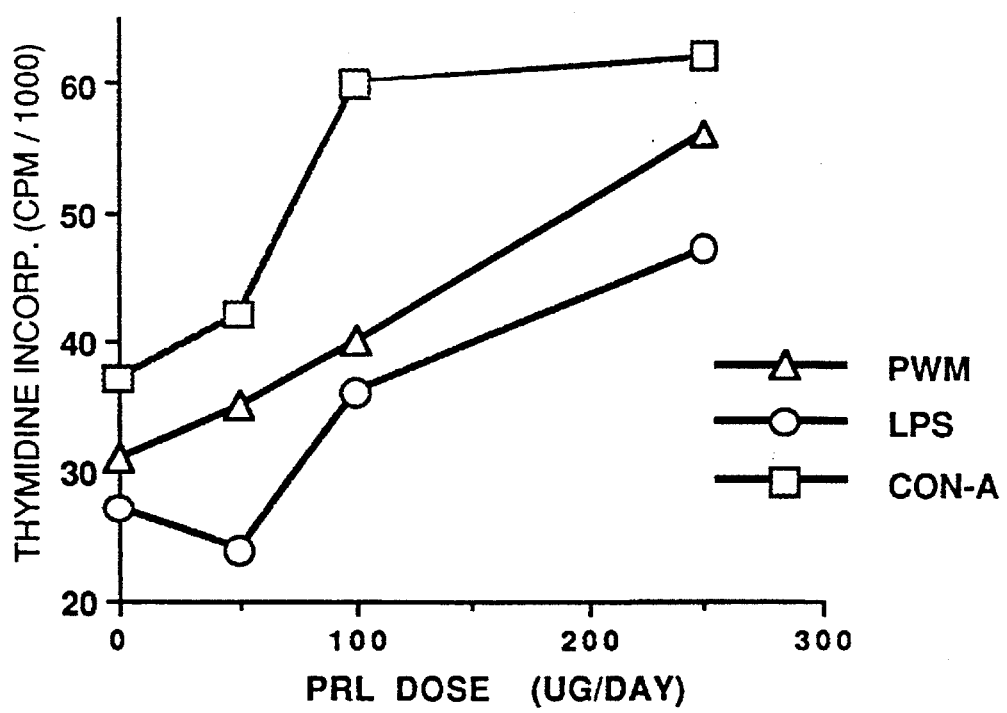
FIG. 10 shows the effect of prolactin on lymphocyte proliferative responses to T and B cell mitogens.

A dose-dependent enhancement of lymphocyte proliferative responses to T and B cell mitogens is demonstrated. (FIG. 10) Note the daily doses effective for immunostimulation when given as a single sc injection are approximately 5- to 10-fold greater (100–250 µg/day vs. 25 µg/day) than those required for affect when infused continually from an implanted minipump (as in FIG. 9 or FIG. 11).

EXAMPLE 7

Figure 11:
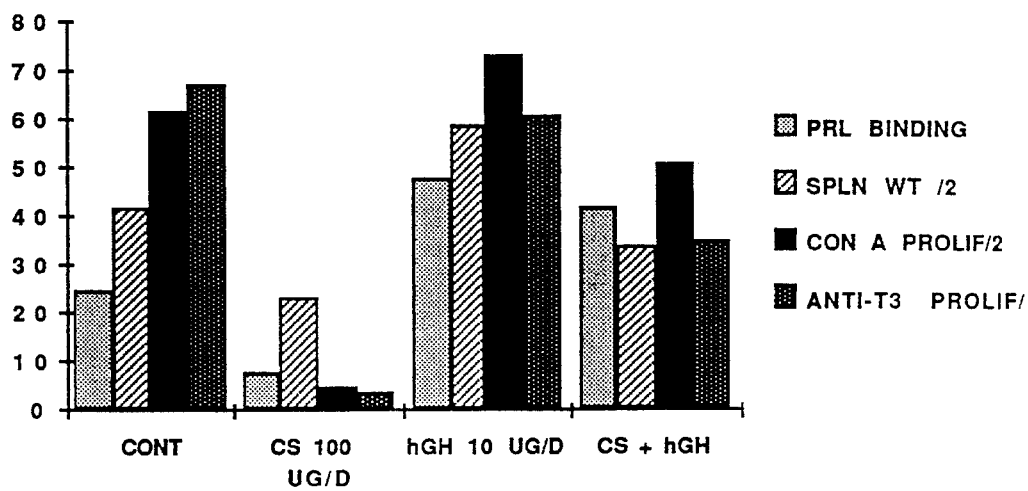
FIG. 11 shows the effects in mice of individual and combined 3 day treatment with corticosterone and recombinant growth hormone on liver prolactin receptor binding, splenocyte proliferation and spleen weight.

Three day treatment of mice with subcutaneous pellets releasing 125 µg per day of corticosterone results in downregulation of prolactin receptors as measured in the liver by prolactin-binding assays. This is closely correlated with suppressed spleen lymphocyte proliferative responses to mitogens. Simultaneous treatment of mice implanted with corticosterone pellets with 25 µg/day of recombinant human growth hormone or ovine prolactin, continually released from implanted osmotic mini-pumps, prevents the downregulation of liver prolactin receptors, and likewise prevents the immunosuppression. Treatment with prolactin or growth hormone alone is seen to dramatically upregulate liver prolactin receptors. This study is pertinent to the mode-of-action proposed above for prolactin agonist treatments. (FIG. 11)

EXAMPLE 8

Groups of four mice are treated with pellets releasing 10, 20, 50, or 200 µg/day of corticosterone. Another group receives 20 µg/day of corticosterone and 25 µg/day of ovine prolactin administered continuously via a subcutaneously implanted osmotic minipump. Two other groups of mice receive either 25 µg/day of ovine prolactin or 20 µg/day of bovine growth hormone, identically administered, as sole treatment.

Following 3 days of treatment, the mice are sacrificed. Serum is taken for determination of serum corticosterone levels by radioimmunoassay. Livers are frozen in liquid nitrogen and specific prolactin and growth hormone binding is quantitated in the liver membrane preps as described in Dave J R, Richardson L L, and Knazek R A, *J. Endocrinology* 99:99–106 (1983). Spleens are immediately disassociated into tissue culture media, and lymphocytes adjusted to equal concentrations and co-cultured with a battery of mitogens, for determination of proliferative responses by radio-thymidine incorporation. Thus, the simultaneously measured endpoints are: a. liver membrane prolactin and GH receptors, b. serum corticosterone, and, c. lymphocyte proliferative responses to mitogens.

Figure 12:
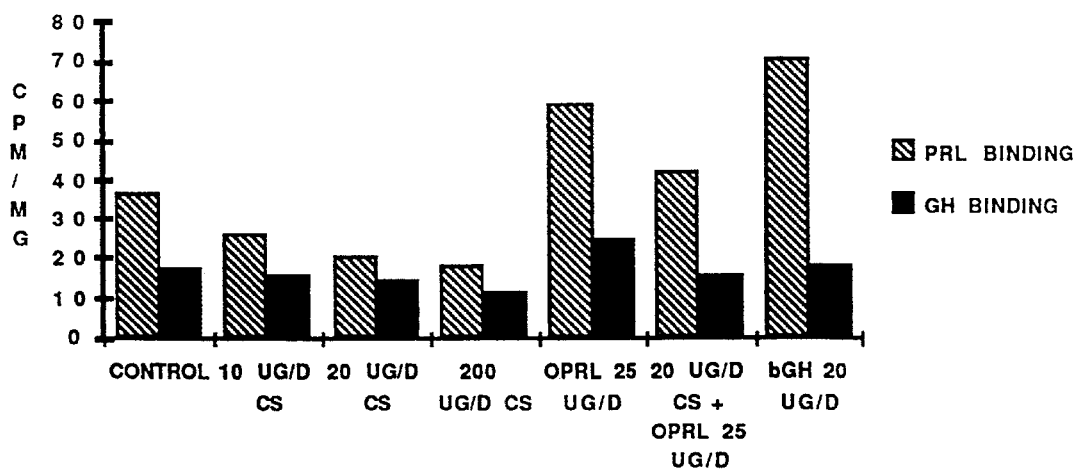
FIG. 12 shows the effects in mice of 3 day treatment with corticosterone, prolactin, and growth hormone on liver specific binding.

Corticosterone treatment results in a dose-dependent downregulation of liver prolactin receptors, proportionate to the elevation of serum corticosterone. Growth hormone or prolactin treatment upregulates liver prolactin receptors, even in mice treated with corticosterone. Treatments are without significant effect on liver growth hormone receptors. (FIG. 12)

Figure 13:
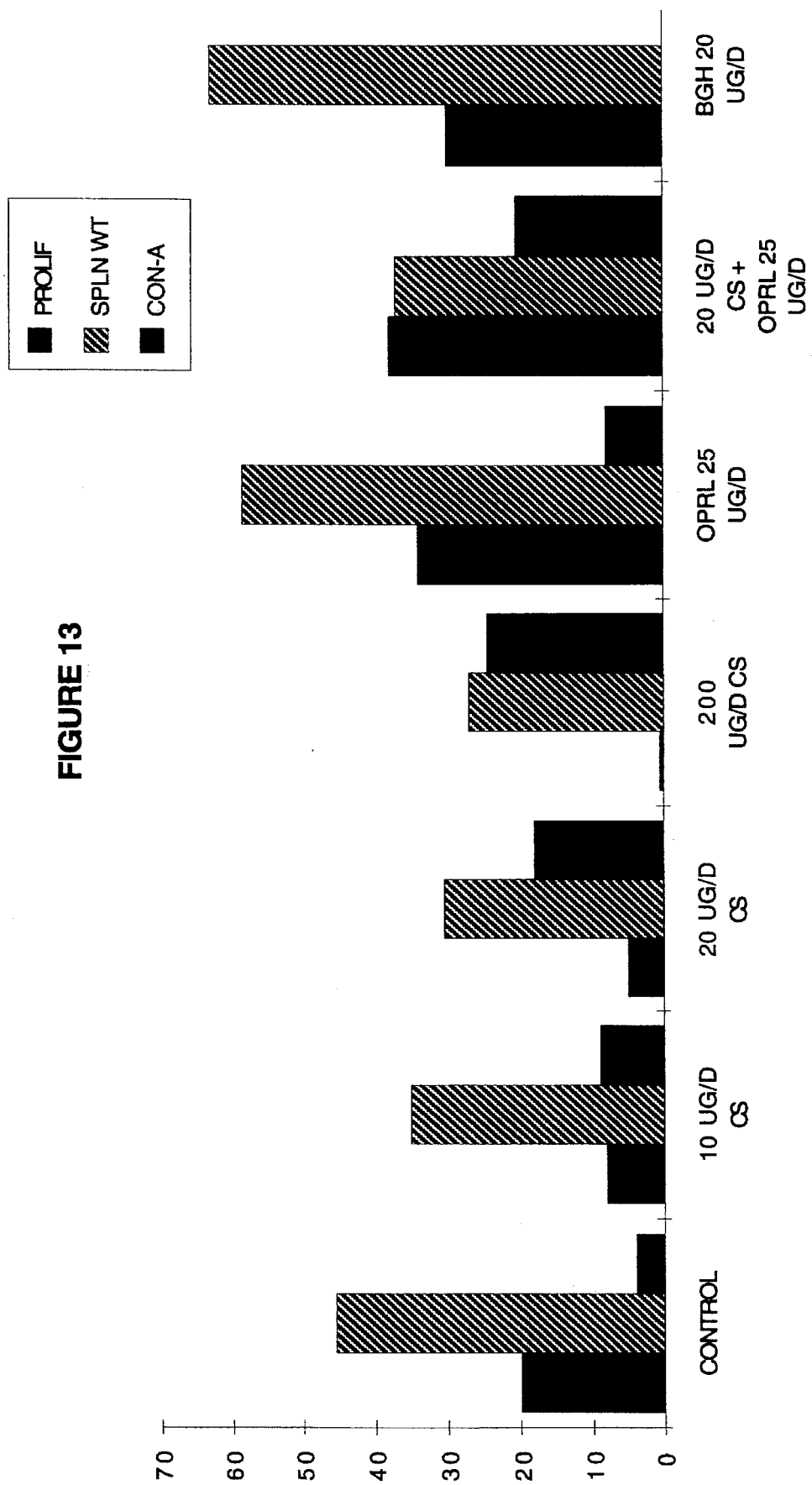
FIG. 13 shows the effects in mice of splenocyte proliferative responses to corticosterone, prolactin and growth hormone in the presence of concanavalin A.

Down regulation of prolactin receptors is associated with decreased spleen proliferative responses to Concanavalin-A. (FIG. 13)

EXAMPLE 9

Figure 14:
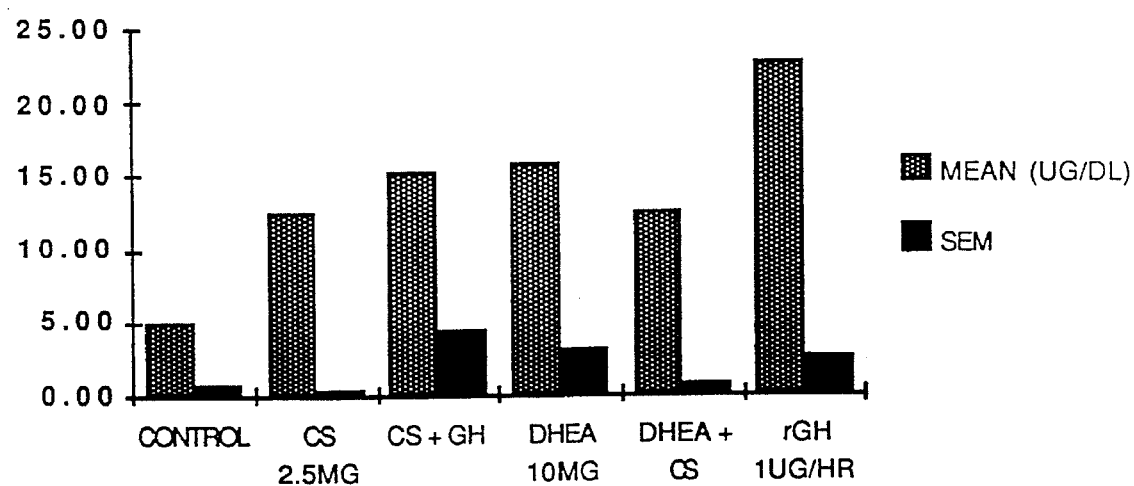
FIG. 14 shows the effect of corticosterone, prolactin or growth hormone on corticosterone blood levels in mice.

Groups of four male mice are treated with pellets releasing 2.5 mg per 20 days (125 µg/day) of corticosterone or with control pellets. Two groups of mice receive either corticosterone in combination with infusion of recombinant human growth hormone at 1 µg/hr (24 µg/day) or growth hormone as sole treatment. Corticosterone treatment results in a 2–3-fold increase in serum corticosterone. Of note, treatment with recombinant growth hormone also results in a dramatic increase in serum corticosterone. (FIG. 14)

Figure 15:
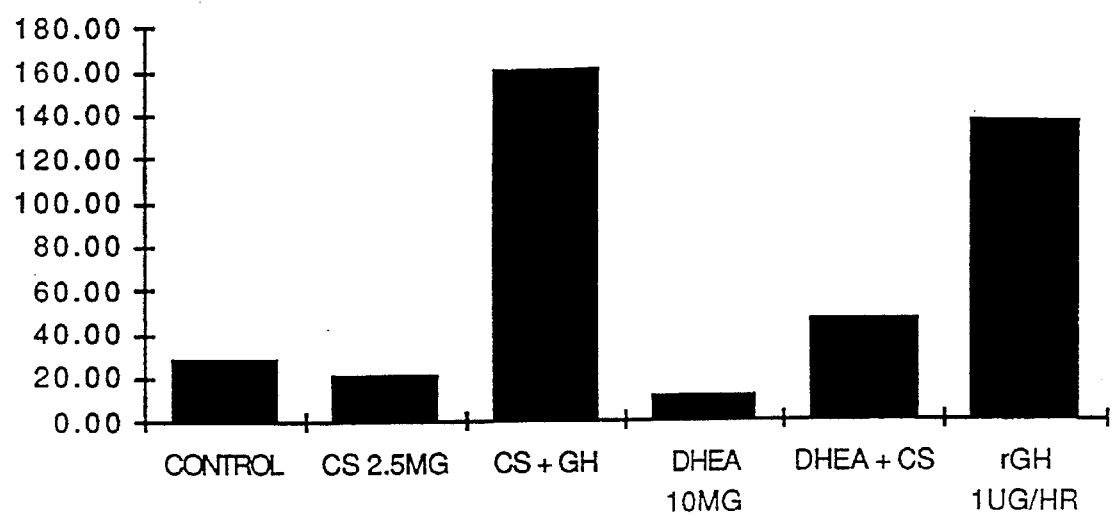
FIG. 15 shows the effect of corticosterone treatment and growth hormone treatment on liver prolactin receptors.

Liver prolactin receptors are seen to be suppressed modestly by corticosterone treatment and greatly upregulated by growth hormone treatment. (FIG. 15) Liver membrane prolactin specific binding is expressed as CPM (in thousands) per mg of protein. The value for each treatment group is the mean of determinations on livers from 3 male mice. In all cases the coefficient of variation within a group is less than 15%.

EXAMPLE 10

Figure 16:
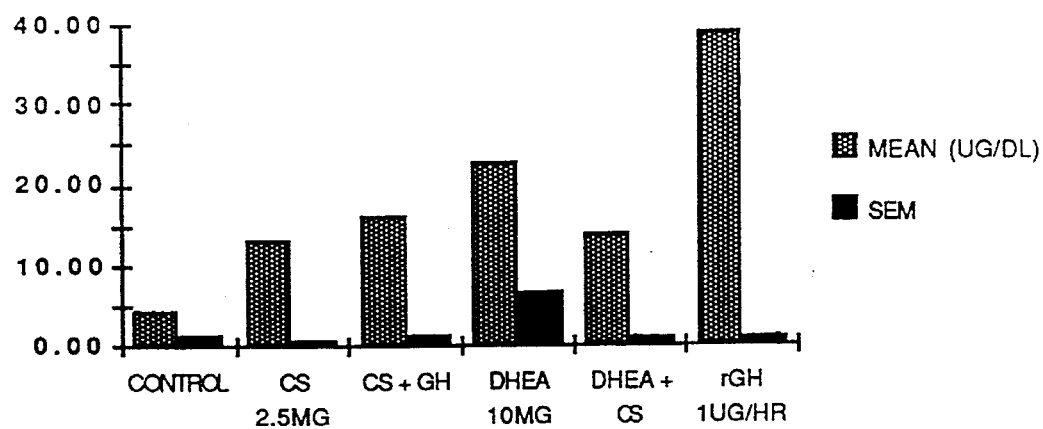
FIG. 16 shows the effect of corticosterone treatment and growth hormone treatment in female mice on serum corticosterone levels.
Figure 17:
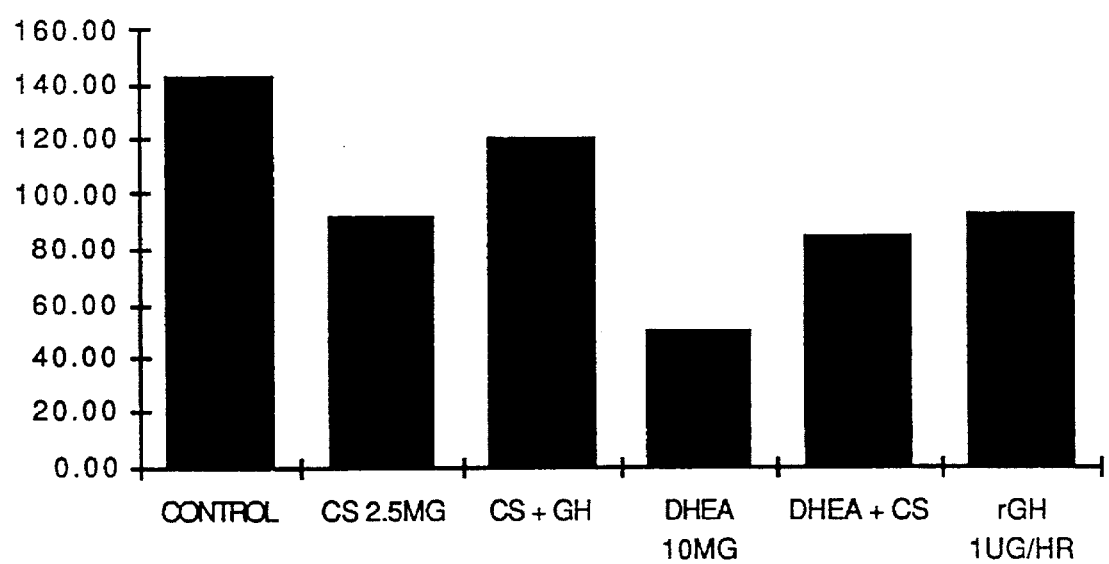
FIG. 17 shows the effect of corticosterone treatment and growth hormone treatment in female mice on liver prolactin receptors.

Groups of four female mice are treated with pellets releasing 2.5 mg per 20 days (125 µg/day) of corticosterone or with control pellets. Two groups of mice receive either corticosterone in combination with infusion of recombinant human growth hormone at 1 µg/hr or growth hormone as sole treatment. Corticosterone treatment results in a 2–3-fold increase in serum corticosterone. Treatment with growth hormone is again found to greatly increase serum corticosterone levels. Increased corticosterone downregulates prolactin receptors. (FIGS. 16 and 17) Growth hormone treatment upregulates prolactin receptors. 1 µg/hr of human growth hormone is found to achieve a steady state serum level of 3–6 ng/ml of human growth hormone in both male and female mice. Corticosterone treatment resulted in suppression of lymphocyte proliferative responses to all mitogens tested, which is reversed by concurrent growth hormone treatment. (FIG. 18)

Figure 18:
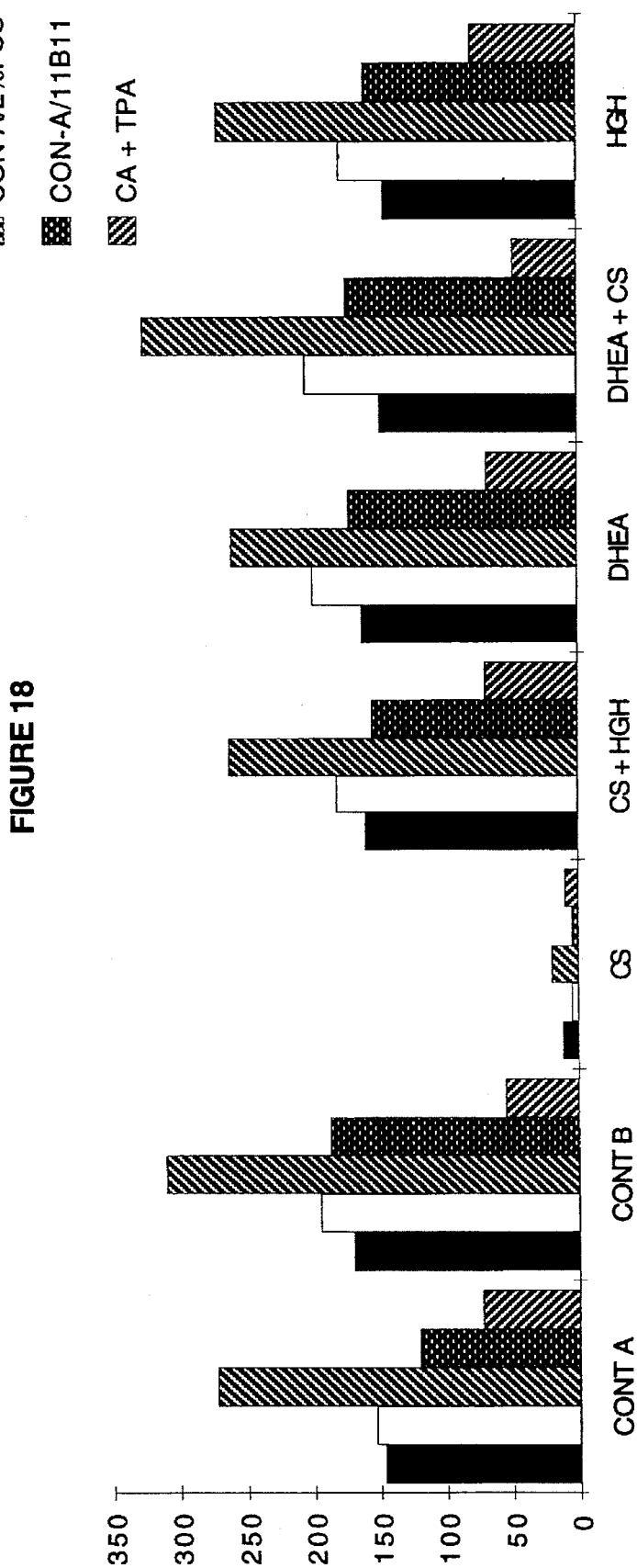
FIG. 18 shows the effect of growth hormone treatment on lymphocyte proliferative responses in lymphocytes from corticosterone treated mice.

In the experiment represented by FIG. 18, spleens from groups of 4 female mice are removed and pooled for co-culture with the mitogens Concanavalin-A (Con-A), antibody to T-cell antibody receptor (anti-T3), or calcium ionophore plus phorbol myristate (Ca+TPA). All cultures are performed in serum free media except for the indicated additions of 2% fetal calf serum (FCS) or 20% hybridoma supernatant containing neutralizing monoclonal antibody to IL-4 ( 11B 11). Tritiated thymidine incorporation is determined after 60 hours in culture. Corticosterone (CS) treatment is 125 µg/day from subcutaneous pellet. Human growth hormone (GH) treatment is 1 µg/hr from implanted osmotic minipump.

EXAMPLE 11

Figure 19:
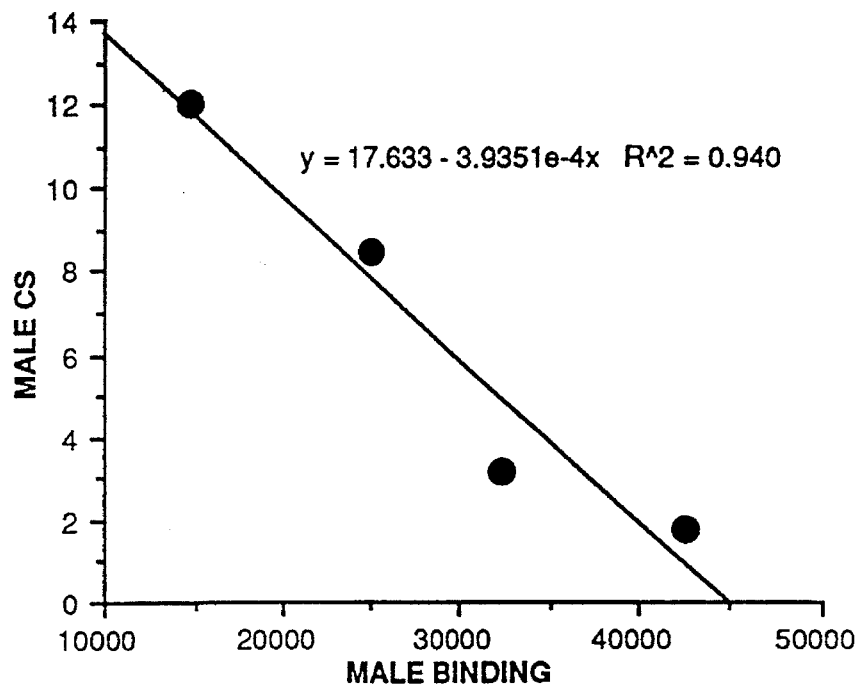
FIG. 19 shows the relationship between male serum corticosterone levels and liver specific prolactin binding.
Figure 20:
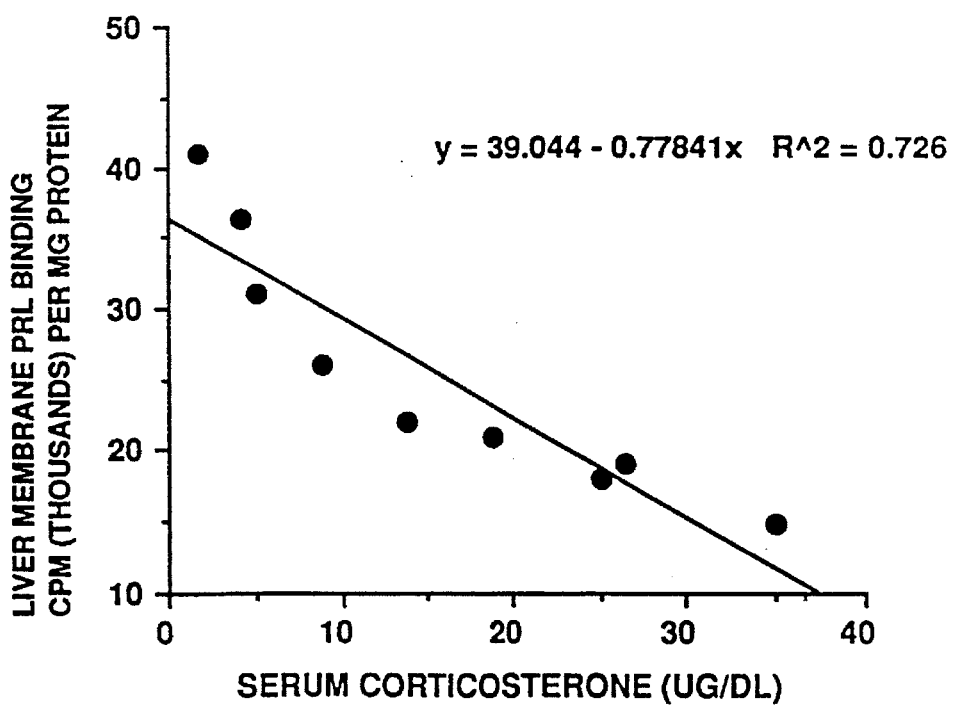
FIG. 20 shows the relationship between serum corticosterone levels and liver specific prolactin binding.

Data from three experiments is expressed as dot plots of serum corticosterone on one axis and liver specific prolactin binding on the other. Each point represents the mean corticosterone value and prolactin binding value on at least 3 mice in a treatment group. Mice are treated for 3 to 4 days with vehicle or varying doses of corticosterone. Mice treated concurrently with prolactin or growth hormone are excluded from analysis, as these treatments markedly upregulate prolactin receptors. A highly significant inverse correlation is seen between serum corticosterone levels and liver specific prolactin binding in each experiment. (FIGS. 19 and 20)

EXAMPLE 12

Figure 21:
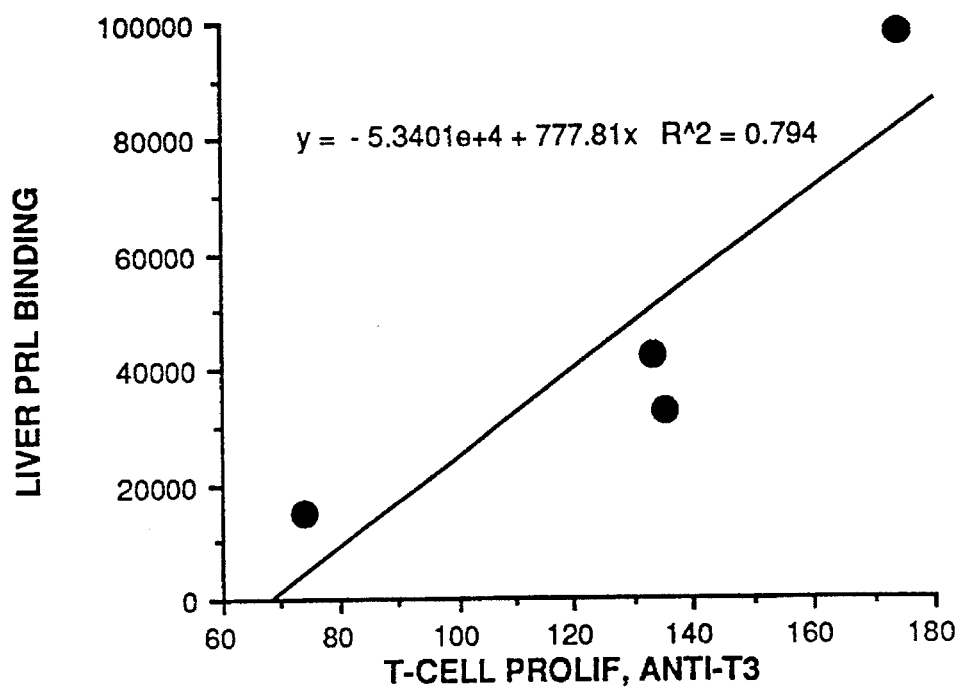
FIG. 21 shows the relationship between T-cell proliferative responses and liver specific prolactin binding.

In FIG. 21, the T-cell proliferative responses to the mitogen anti-T3 monoclonal Ab show a significant positive correlation with the liver specific prolactin binding. Mean values for lymphocyte radio-thymidine uptake and prolactin binding are plotted for 4 groups of mice treated with vehicle, corticosterone 50 µg/day, human growth hormone, 24 µg/day, and corticosterone and growth hormone.

Figure 22:
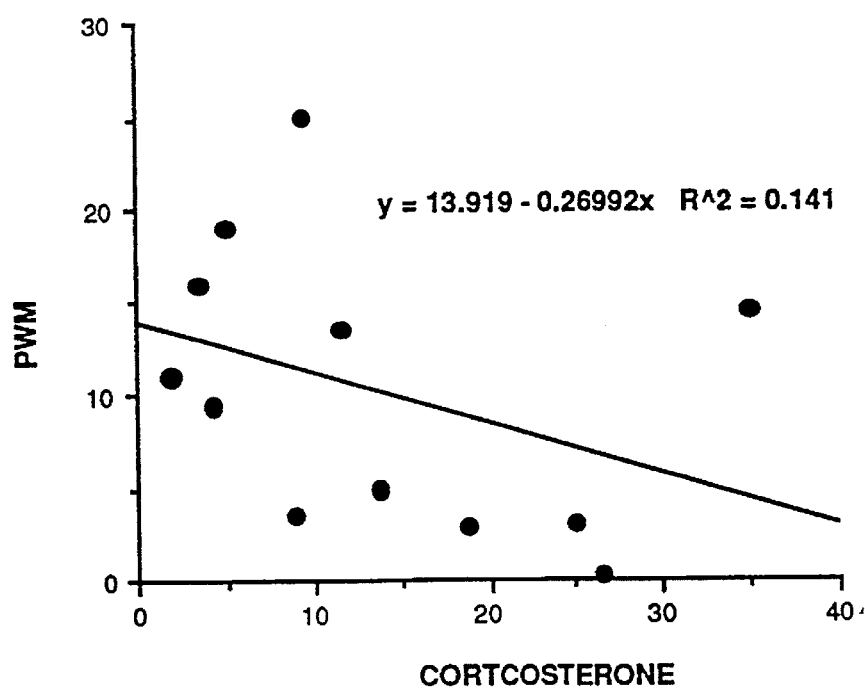
FIG. 22 shows the relationship between lymphocyte proliferation and treatments of mice with chronic stressors resulting in varying elevations of corticosterone levels, with or without concurrent treatment with ovine prolactin.
Figure 23:
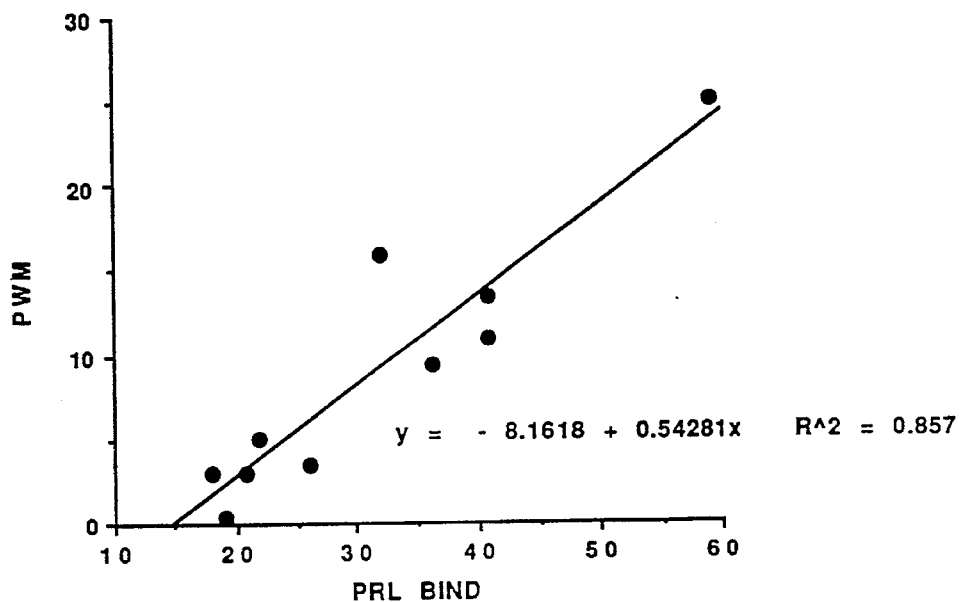
FIG. 23 shows the relationship between lymphocyte proliferation and liver specific prolactin binding.

In FIG. 22, groups of 3 to 4 male mice received a variety of treatments or chronic stressors resulting in varying elevations of corticosterone levels, with or without concurrent treatment with ovine prolactin. Each point represents the mean proliferative response to poke weed mitogen (PWM) and the mean serum corticosterone. It can be seen that corticosterone correlates poorly with lymphocyte proliferation due to the fact that high corticosterone does not result in suppression in prolactin-treated mice. In contrast, when the liver specific prolactin binding is plotted against lymphocyte proliferation in the same groups of mice, the positive correlation is significant (r=0.857, p<0.05). (FIG. 23) This data indicates that down regulation of prolactin receptors by corticosterone is a primary mechanism by which they alter lymphocyte function in vivo.

EXAMPLE 13

Figure 24:
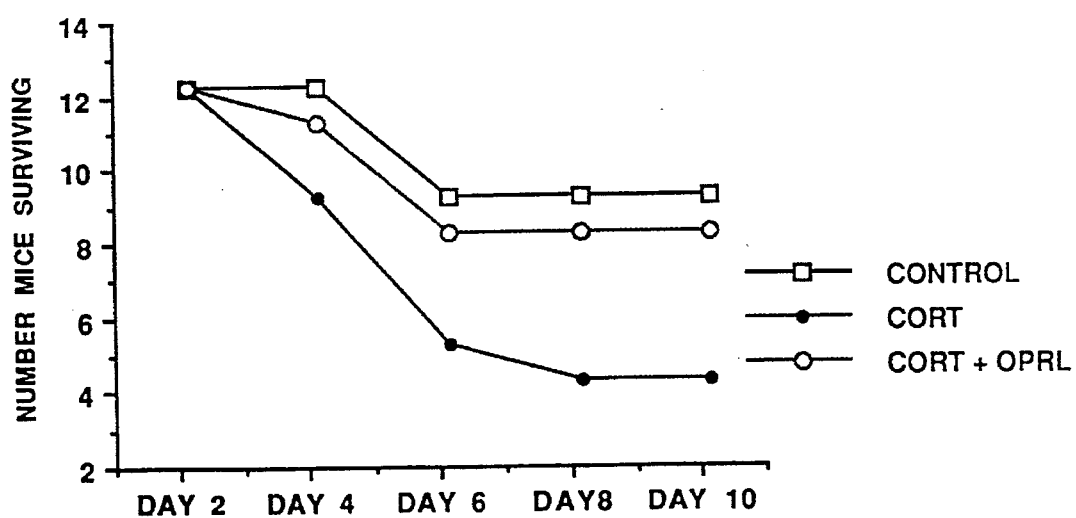
FIG. 24 shows the results of *L. monocytogenes* challenge to mice treated with corticosterone or corticosterone plus prolactin.

FIG. 24 illustrates that treatment of mice with corticosterone increases lethality of infection with the pathogenic bacteria, *Listeria monocytogenes*. Groups of 12 male C3H/HeN male mice, specific pathogen free and barrier-maintained, are injected intraperitoneally with an approximately LD 20 dose of *L. monocytogenes*. Mice are implanted with Azlet minipumps delivering 0.5 µl of liquid per hour for seven days. Animals received either 24 µg/day of bovine serum albumin (Control), 50 µg/day of corticosterone and 24 µg/day of serum albumin (Cort), or 50 µg/day of corticosterone and 24 µg/day of ovine prolactin (Cort+oPRL). Survival of mice is tabulated over 10 days. No deaths occurred after day 8.

Clearance of listerial infection requires macrophages to be activated to become bactericidal. This process in turn depends on a specific T-cell response resulting in secretion of gamma-interferon, a macrophage activating factor. Secretion of gamma-interferon by T-lymphocytes is known to be inhibited by corticosteroids, which results, in vivo, in increased lethality following infection. Mice treated concurrently with corticosterone and ovine prolactin show a significantly decreased lethality compared to corticosterone treatment alone. Thus, the prolactin treatment protects against increased susceptibility to infection due to elevated serum levels of corticosteroids.

We claim:

1. A method for stimulating lymphocyte proliferation in a human having suppressed lymphocyte function comprising administering to the human an amount of a prolactin agonist effective to stimulate lymphocyte proliferation.

2. The method of claim 1, wherein the lymphocyte function is suppressed by stress.

3. The method of claim 1, wherein the lymphocyte function is suppressed by glucocorticosteroids.

4. The method of claim 1, wherein the prolactin-agonist is selected from the group consisting of natural prolactin, recombinant prolactin, and active peptide sequences from prolactin.

5. A method for stimulating lymphocyte proliferation in an animal having suppressed lymphocyte function comprising administering to the animal an amount of a prolactin agonist effective to stimulate lymphocyte proliferation.

6. The method of claim 5, wherein the lymphocyte function is suppressed by stress.

7. The method of claim 5, wherein the lymphocyte function is suppressed by glucocorticosteroids.

8. The method of claim 5, wherein the prolactin-agonist is selected from the group consisting of natural prolactin, recombinant prolactin, and active peptide sequences from prolactin.

9. The method of claim 1, wherein the lymphocyte function is suppressed by an opioid.

10. The method of claim 1, wherein the lymphocyte function is suppressed by radiation or chemotherapy.

11. The method of claim 1, wherein the lymphocyte function is suppressed by natural corticosteroid or a recombinant or synthetic analog of corticosteroid.

12. The method of claim 1, wherein the prolactin agonist is natural prolactin or a recombinant or synthetic analog of prolactin.

13. The method of claim 1, wherein the prolactin agonist is natural growth hormone or a recombinant or synthetic analog of growth hormone.

14. The method of claim 1, further comprising administering a mitogen with the prolactin agonist.

15. The method of claim 5, wherein the lymphocyte function is suppressed by an opioid.

16. The method of claim 5, wherein the lymphocyte function is suppressed by radiation or chemotherapy.

17. The method of claim 5, wherein the lymphocyte function is suppressed by natural corticosteroid or a recombinant or synthetic analog of corticosteroid.

18. The method of claim 5, wherein the prolactin agonist is natural prolactin or a recombinant or synthetic analog of prolactin.

19. The method of claim 5, wherein the prolactin agonist is natural growth hormone or a recombinant or synthetic analog of growth hormone.

20. The method of claim 5, further comprising administering a mitogen with the prolactin agonist.

* * * * *